(12) United States Patent
Trowe

(10) Patent No.: US 9,134,325 B2
(45) Date of Patent: Sep. 15, 2015

(54) RESISTANCE BIOMARKERS FOR HDAC INHIBITORS

(71) Applicant: Celgene Corporation, Summit, NJ (US)

(72) Inventor: Torsten Bernhard Trowe, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/019,456

(22) Filed: Sep. 5, 2013

(65) Prior Publication Data

US 2014/0073587 A1 Mar. 13, 2014
US 2014/0256650 A2 Sep. 11, 2014

Related U.S. Application Data

(60) Provisional application No. 61/784,501, filed on Mar. 14, 2013, provisional application No. 61/726,464, filed on Nov. 14, 2012, provisional application No. 61/698,341, filed on Sep. 7, 2012.

(51) Int. Cl.
G01N 33/574 (2006.01)
G01N 33/68 (2006.01)
A61K 38/15 (2006.01)

(52) U.S. Cl.
CPC ............ G01N 33/6893 (2013.01); A61K 38/15 (2013.01); G01N 33/574 (2013.01)

(58) Field of Classification Search
None
See application file for complete search history.

(56) References Cited

U.S. PATENT DOCUMENTS

| | | | |
|---|---|---|---|
| 4,328,245 A | 5/1982 | Yu et al. |
| 4,409,239 A | 10/1983 | Yu et al. |
| 4,410,545 A | 10/1983 | Yu et al. |
| 4,977,138 A | 12/1990 | Okuhara et al. |
| 5,510,270 A | 4/1996 | Fodor et al. |
| 5,545,522 A | 8/1996 | Van Gelder et al. |
| 5,556,752 A | 9/1996 | Lockhart et al. |
| 5,578,832 A | 11/1996 | Trulson et al. |
| 5,605,793 A | 2/1997 | Stemmer |
| 5,716,785 A | 2/1998 | Van Gelder et al. |
| 5,776,905 A | 7/1998 | Gibbons et al. |
| 5,830,721 A | 11/1998 | Stemmer et al. |
| 5,837,458 A | 11/1998 | Minshull et al. |
| 5,891,636 A | 4/1999 | Van Gelder et al. |
| 6,117,679 A | 9/2000 | Stemmer |
| 6,350,458 B1 | 2/2002 | Modi et al. |
| 6,391,640 B1 | 5/2002 | Minshull et al. |
| 6,403,555 B1 | 6/2002 | Skov et al. |
| 6,548,479 B1 | 4/2003 | Skov et al. |
| 6,706,686 B2 | 3/2004 | Long et al. |
| 6,777,217 B1 | 8/2004 | Schreiber et al. |
| 6,809,118 B2 | 10/2004 | Chung et al. |
| 6,828,302 B1 | 12/2004 | Skov |
| 6,905,669 B2 | 6/2005 | DiMartino |
| 6,946,441 B2 | 9/2005 | Long et al. |
| 7,041,639 B2 | 5/2006 | Skov |
| 7,056,883 B2 | 6/2006 | Ito et al. |
| 7,056,884 B2 | 6/2006 | Nakajima et al. |
| 7,148,204 B2 | 12/2006 | Bennett et al. |
| 7,171,311 B2 | 1/2007 | Dai et al. |
| 7,314,862 B2 | 1/2008 | Naoe et al. |
| 7,354,928 B2 | 4/2008 | Wang et al. |
| 7,396,665 B2 | 7/2008 | Ueda et al. |
| 7,470,722 B2 | 12/2008 | Malecha et al. |
| 7,488,712 B2 | 2/2009 | Yoshida et al. |
| 7,608,280 B2 | 10/2009 | Ueda et al. |
| 7,611,724 B2 | 11/2009 | Ueda et al. |

(Continued)

FOREIGN PATENT DOCUMENTS

| | | |
|---|---|---|
| CA | 2317003 | 8/2001 |
| EP | 0352646 | 1/1990 |

(Continued)

OTHER PUBLICATIONS

Aron et al., "Depsipeptide (FR901228) induces histone acetylation and inhibition of histone deacetylase in chronic lymphocytic leukemia cells concurrent with activation of caspase 8-mediated apoptosis and down- regulation of c-FLIP protein," Blood, 102(2):652-658 (2003).
Bates et al., "Final Clinical Results of a Phase 2 NCI Multicenter Study of romidepsin in Recurrent Cutaneous T-Cell Lymphoma (Molecular Analyses Included)," ASH Annual Meeting Abstracts, 112(11): p. 1568 (2008).
Bates et al., "Laboratory correlates for a phase II trial of romidepsin in cutaneous and peripheral T-cell lymphoma ," Br J Haematol 148:256 (2010).
Berge et al., "Pharmaceutical Salts," J Pharm Science 66:1-19, 1977.
Bhalla, "Epigenetic and chromatin modicifers as targeted therapy of hematologic malignancies," J Clin Oncol, 23(17):3971-3993 (2005).
Bishton et al., "Epigenetic target in hematological malignancies: combination therapies with HDAC's and demethylating agents," Expert Rev Anticancer Ther, 7(10):1439-1449 (2007).

(Continued)

Primary Examiner — Misook Yu
Assistant Examiner — Nelson B Moseley, II
(74) Attorney, Agent, or Firm — Jones Day

(57) ABSTRACT

Provided herein are methods for identifying a cancer patient at risk for resistance to an HDAC inhibitor therapy, comprising obtaining a tumor sample from the cancer patient; detecting the presence of Testis-specific Y-encoded-like protein 5 (TSPYL5) expression in the sample; quantifying a level of the TSPYL5 expression in the sample, wherein a high level of the TSPYL5 expression, relative to a defined expression threshold of the TSPYL5, correlates with resistance to the HDAC inhibitor therapy; and applying the correlation to identify the cancer patient at risk for resistance to the HDAC inhibitor therapy. Also provided is a method for identifying a cancer patient with an increased likelihood of a positive clinical response to an HDAC inhibitor therapy comprising obtaining a tumor sample from the cancer patient; detecting the presence of Testis-specific Y-encoded-like protein 5 (TSPYL5) expression in said sample; quantifying a level of said TSPYL5 expression in said sample, wherein a low level of the TSPYL5 expression, relative to a defined expression threshold of the TSPYL5, identifies said cancer patient with an increased likelihood of a positive clinical response to said HDAC inhibitor therapy. Related methods and compositions are also provided.

3 Claims, 8 Drawing Sheets

(56) References Cited

U.S. PATENT DOCUMENTS

| | | |
|---|---|---|
| 7,857,804 B2 | 12/2010 | McCaffrey et al. |
| 2003/0162293 A1 | 8/2003 | Chu et al. |
| 2004/0018968 A1 | 1/2004 | Sgouros et al. |
| 2004/0053820 A1 | 3/2004 | Nakajima et al. |
| 2004/0072735 A1 | 4/2004 | Richon et al. |
| 2004/0077591 A1 | 4/2004 | Dangond |
| 2004/0127523 A1 | 7/2004 | Bacopoulos et al. |
| 2004/0228909 A1 | 11/2004 | Sarris et al. |
| 2005/0059682 A1 | 3/2005 | Rubinfeld |
| 2005/0070467 A1 | 3/2005 | Naoe et al. |
| 2005/0187148 A1 | 8/2005 | Naoe et al. |
| 2005/0187149 A1 | 8/2005 | Naoe et al. |
| 2005/0191713 A1 | 9/2005 | Sasakawa et al. |
| 2005/0222013 A1 | 10/2005 | Jung et al. |
| 2005/0272647 A1 | 12/2005 | Yamaji et al. |
| 2006/0018921 A1 | 1/2006 | Levenson et al. |
| 2006/0019883 A1 | 1/2006 | Kronblad et al. |
| 2006/0100140 A1 | 5/2006 | Dent et al. |
| 2006/0106049 A1 | 5/2006 | Odenike |
| 2006/0128660 A1 | 6/2006 | Rajski et al. |
| 2006/0135413 A1 | 6/2006 | Naoe et al. |
| 2006/0223747 A1 | 10/2006 | Ito et al. |
| 2006/0270016 A1 | 11/2006 | Holm |
| 2007/0015787 A1 | 1/2007 | Bruncko et al. |
| 2007/0110719 A1 | 5/2007 | Holm |
| 2007/0129290 A1 | 6/2007 | Or et al. |
| 2007/0148228 A1 | 6/2007 | Cumming et al. |
| 2007/0292512 A1 | 12/2007 | Leonard et al. |
| 2008/0214446 A1 | 9/2008 | Okada et al. |
| 2008/0233562 A1 | 9/2008 | Sasakawa et al. |
| 2009/0186382 A1 | 7/2009 | Verdine et al. |
| 2009/0209616 A1 | 8/2009 | Verdine et al. |
| 2009/0221473 A1 | 9/2009 | Chan et al. |
| 2010/0093610 A1 | 4/2010 | Vrolijk et al. |
| 2012/0046442 A1 | 2/2012 | Hanko et al. |

FOREIGN PATENT DOCUMENTS

| | | |
|---|---|---|
| EP | 1010705 | 6/2000 |
| EP | 1426054 | 6/2004 |
| JP | 1995-64872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 01/18171 | 3/2001 |
| WO | WO 01/42282 | 6/2001 |
| WO | WO 02/06307 | 1/2002 |
| WO | WO 02/015921 | 2/2002 |
| WO | WO 02/20817 | 3/2002 |
| WO | WO 02/86498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/129105 | 12/2006 |
| WO | WO 2007/009539 | 1/2007 |
| WO | 2007040522 | 4/2007 |
| WO | WO 2007/040522 | 4/2007 |
| WO | WO 2007/058896 | 5/2007 |
| WO | WO 2007/061939 | 5/2007 |
| WO | WO 2007/067476 | 6/2007 |
| WO | WO 2007/145704 | 12/2007 |
| WO | WO 2007/146730 | 12/2007 |
| WO | WO 2008/013589 | 1/2008 |
| WO | WO 2008/095050 | 8/2008 |
| WO | WO 2010/047714 | 4/2010 |
| WO | WO 2013/158984 | 10/2013 |

OTHER PUBLICATIONS

Bogden et al., "Growth of Human Tumor Xenografts Implanted under the Renal Capsule of Normal Immunocompetent Mice," Exp Cell Biol 47:281-293 (1979).

Bolden et al., "Anticancer activities of histone deacetylase inhibitors," Nat Rev Drug Discovery, 5(9):769-784 (2006).

Bradner et al., "Chemical phylogenetics of histone deacetylases," Nat Chem Biol 6:238 (2010).

Budillon et al., "Growth arrest, apoptosis and potentiation of 5-fluorouracil and Raltitrexed cytotoxic effect induced by histone deacetylase inhibitor SAHA in colorectal cancer cells," Eur J Cancer 38:S29 (2002).

Burger's Medicinal Chemistry and Drug Discovery, 172-178, 949-982 (Manfred E. Wolff ed., 5th ed. 1995).

Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).

Byrd et al., "A phase 1 and pharmacodynamic study of depsipeptide (FK228) in chronic lymphocytic leukemia and acute myeloid leukemia," Blood, 105(3):959-967 (2005).

Byrd et al., "Depsipeptide (FR901228): a novel therapeutic agent with Selective in vitro activity against human B-cell chronic lymphocytic leukemia cells ," Blood, 94(4):1401-1408 (1999).

Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).

Chan et al., "Depsipeptide (FR901228, NSC-630176) pharmacokinetics in the rat by LC/MS/MS ," Invest New Drugs,15(3):195-206 (1997).

Cheson et al., "New Drugs for the Treatment of Chronic Lymphocytic Leukemia," Reviews Clin Exp Hematol 4(2):145-166 (2000).

Conway et al., "Vincristine-and Cisplatin-induced Apoptosis in Human Retinoblastoma. Potentiation by Sodium Butyrate," Eur J Cancer, 34(11):1741-1748 (1998).

Dai et al., "Interactions between bortezomib and romidepsin and belinostat in chronic lymphocytic leukemia cells ," Clin Cancer Res, 14(2):549-558 ( 2008).

(56) References Cited

OTHER PUBLICATIONS

Database Biosis 'Online, AN-PREV200400024248, XP-002342749, "Anti-Tumor Efficacy of Four Different Histone Deacetylase Inhibitors on Hepatoma Cells in Vitro", 2003 (Abstract No. T1786).

Dokmanovic & Marks, "Prospects: histone deacetylase inhibitors ," J Cell Biochem, 96(2):293-304 (2005).

Epping et al., "TSPYL5 suppresses p53 levels and function by physical interaction with USP7," Nature Cell Biol 13:102 (2011).

Fiebig et al., "Bcl-XL is qualitatively different from and ten times more effective than Bcl-2 when expressed in a breast cancer cell line," Cancer, 6:213 (2006).

Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).

Finnin et al., "Structures of a histone deacetylase homologue bound to the TSA and SAHA Inhibitors," Nature, 401(6749):188-193 (1999).

Fischer et al., 41$^{st}$ Annual Meeting of the American Society of Clinical Oncology, Abstr # 3106 (2005).

Fotheringham et al., "Genome-wide Loss-of-Function Screen Reveals an Important Role for the Proteasome in HDAC Inhibitor-Induced Apoptosis ," Cancer Cell 15:57 (2009).

Fukumura et al., "A sensitive transcriptome analysis method that can detect unknown transcripts," Nucl Acids Res 31(16):e94 (2003).

Furumai et al.,"FK228 (depsipeptide) as a natural prodrug that inhibits class I histone deacetylases," Cancer Res, 62(17):4916-4921 (2002).

Garcia-Manero et al., "Phase ½ study of the combination of 5-aza-2'-deoxycytidine with valporic acid inpatients with leukemia ," Blood, 108(10):3271-3279 (2006).

Geldof et al., "Cytotoxicity and neurocytoxicity of new marine anticancer agents evalucated using in vitro assays," Cancer Chemother & Pharmacol 44(4):312-318 (1999).

Gore et al., "Combined DNA methyltransferase and histone deacetylase inhibition in the treatment of myeloid neoplasms," Cancer Res, 66(12):6361-6369 (2006).

Gore et al., "Impact of the putative differentiating agent sodium phenylbutyrate on myelodysplastic syndromes and acute myeloid leukemia ," Clin Cancer Res, 7(8):2330-2339 (2001).

Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).

Harrison et al., "High Response Rates with the Combination of Bortezomib, Dexamethasone and the Pan-Histone Deacetylase Inhibitor Romidepsin in Patients with Relapsed or Refractory Multiple Myeloma in Phase I/II Clinical Trial," ASH Annual Meeting Abstracts, 112(11):3698 (2008).

Inoue et al., "Subrenal capsule assay-an experimental study and clinical application to chemosensitivity tests," Gan to Kagaku Ryoho 14(5Pt2):1629-1635 (1987) (Abstract).

Jones & Baylin, "The Epigenomics of Cancer," Cell 128:683-692 (2007).

Jones & Baylin, "The fundamental role of epigenetic events in Cancer,"Nat Rev Genet, 3(6):415-428 (2002).

Jung et al., "Amide Analogues of Trichostatin A as Inhibitors of Histone Deacetylase and Inducers of Terminal Cell Differentiation," J Med Chem US 42(22):4669-4679 (1999).

Jung et al., "Gene silencing of TSPYL5 mediated by aberrant promoter methylation in gastric cancers ," Lab Invest 88:153(2008).

Kahn et al., "Total Synthesis of the Antitumor Depsipeptide FR-901,228," J Am Chem Soc 118:7237-7238, (1996).

Kano et al., "The Joint Meeting of the 64$^{th}$ Annual Meeting of the Japanese Society of Hematology and the 44$^{th}$ Annual Meeting of the Japanese Society of Clinical Hematology," Japanese J Clin Hematology 43(8):116 (2002).

Kawamoto et al., "Expression Profiling by iAFLP: A PCR-Based Method for Genome-Wide Gene Expression Profiling," Genome Res 12:1305-1312 (1999).

Khan et al., "Analysis of histone deacetylase inhibitor, depsipeptide (FR901228), effect on multiple myeloma ," Br J Haematol, 125(2):156-161 (2004).

Khan et al., "HR23B is a biomarker for tumor sensitivity to HDAC inhibitor-based therapy ," PNAS 107:6532 (2010).

Kim et al., "Clinically significant responses Achieved with Romidepsin in Treatment-Refractory Cutaneous T-Cell Lymphoma: Final Results from a Phase 2B, International, Multicenter, Registration Study," ASH Annual Meeting Abstracts, 112(11):263 (2008).

Kim et al., "TSPYL5 is involved in cell growth and the resistance to radiation in A549 cells via the regulation of p21WAF1/Cip1 and PTEN/AKT pathway ," Biochem and Biophys Res Comm 392:448 (2010).

Kim et al., "Epigenomic Profiling Reveals Novel and Frequent Targets of Aberrant DNA Methylation-Mediated Silencing in Milignant Glioma," Cancer Res 66:7490 (2006).

Kisselev & Goldberg, "Proteasome inhibitors: from research tools to drug candidates," Chem Biol 8:739-758 (2001).

Kitazono et al., "Adenovirus HSV-TK Constuct with Thyroid-Specific Promoter: Enhancement of Activity and Specificity with Histone Deacetylase Inhibitors and Agents Modulating the Camp Pathway," Int J Cancer 99:453-459 (2002).

Kitazono et al., "Enhanced Adenovirus Transgene Expression in Malignant Cells Treated with the Histone Deacetylase Inhibitor FR901228," Cancer Res 61:6328-6330 (2001).

Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).

Kitazono et al., Proc Amer Assoc Cancer Res Annual 43:799 (2002) (Abstract only).

Klimek et al., "Tolerability, pharmacodynamics, and pharmacokinetics studies fo depsipeptide (romidepsin) in patients with acute myelogenous leukemia or advanced myelodysplastic syndromes," Clin Cancer Res, 14(3):826-832 (2008).

Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).

Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).

Kosugi et al., "In vivo Effects of a Histone Deacetylase Inhibitor, FK228, on Human Acute Promyelocytic Leukemia in NOD/Shi-scid/scid Mice," Japanese J Cancer Res 92(5):529-536 (2001).

Kuendgen et al., "Treatment of myelodysplastic syndromes with valproic acid alone or in combination with all-trans retinoic acid," Blood, 104(5):1266-1269 (2004).

Liakopoulou et al., "Stimulation of Fetal Hemoglobin Production by Short Chain Fatty Acids," Blood, 86:3227 (1995).

Maeda et al., "Up-regulation of costimulatory/adhesion molecules by histone deacetylase ihibitors in acute myeloid leukemia cells," Blood, 96(12):3847-3856 (2000).

Magner et al., "Activation of MHC class I, II, and CD40 gene expression by histone deacetylose inhibitors ," J Immunol, 165(12):7017-7024 (2000).

Marks et al., "Histone deacetylase inhibitors: Inducers of differentiation or apoptosis of transformed cells," J Natl Cancer Inst, 92(15):1210-1216 (2000).

Marshall et al., "A phase I trial of depsipeptide (FR901228) in patients with advanced cancer ," J Exp Ther Oncol, 2(6):325-332 (2002).

Mertins et al., Proc Amer Assoc Cancer Res Annual Meetins 40:623 (1999).

Mitsiades et al., "Transcriptional signature of histone deacetylase inhibition in multiple myeloma: biological and clinical implications," Proc Natl Acad Sci USA, 101(2):540-545 (2004).

Molife et al.,"Phase II study of FK228 in patients with hormone refractory prostate cancer (HRPC)," J Clin Oncol (Meeting Abstracts), 24(18 Suppl):14554 (2006).

Murata et al., "Apoptotic Cytotoxic Effects of a Histone Deacetylase Inhibitor, FK228, on Malignant Lymphoid Cells," Japanese J Cancer Res 91:1154-1160 (2000).

(56) References Cited

OTHER PUBLICATIONS

Nakajima et al., ", FR901228, a potent antitumor antibiotic, is a novel histone det1cetylose inhibitor," Exp Cell Res, 241(1)126-133 (1998).
Nebbioso et al., "Tumor-selective action of HDAC inhibitors involves TRAIL induction in acute myeloid leukemia cells," Nat Med, 11(1):77-84 (2005).
Nebozhyn et al., "Quantitative PCR on 5 genes reliably Identifies CTCL patients with 5% to 99% circulating tumor cells with 90% accuracy," Blood, 107(8):3189-3196 (2006).
Newbold et al., "Characterisation of the novel apoptotic and therapeutic activities of the histone deacetylase inhibitor romidepsin," Mol Cancer Ther, 7(5):1066-1079 (2008).
Niesvizky et al., "Multicenter Phase II Trial of the Histone Deacetylase Inhibitor Depsipeptide (FK228) for the Treatment of Relapsed or Refractory Multiple Myeloma (MM)," Blood ASH Annual Meeting Abstracts, 106(11):2574 (2005).
Nishimura et al., "A New Antitumor Antibiotic, FE900840," J Antibiot XLII(4):553-557 (1989).
Nuijen et al., "Development of a lyophilized parenteral pharmaceutical formulation the investicational polypeptide marine anticancer agent kahalalide F.," Medline (2001) XP-002206588.
Odenike et al., "Histone deacetylase inhibitor romidepsin has differential activity in core binding factor acute myeloid leukemia," Cancer Res, 14(21):7095-7101 (2008).
Paoluzzi et al., "Romidepsin and belinostat synergize the antineoplastic effect of bortezomib in mantle cell lymphoma," Clin Cancer Res, 16(2):554-565 (2010).
Peart et al., "Identification and functional significance of genes regulated by structurally different histone deacetylose inhibitors ," Proc Natl Acad Sci USA, 102(10):3697-3702 (2005).
Peart et al., "Novel mechanisms of apoptosis induced by histone deacetylase inhibitors ," Cancer Res, 63(15):4460-4471 (2003).
Pei et al., "Synergistic induction of oxidative injury and apoptosis in human multiple myeloma cells by the proteasome inhibitor bortezpmib and histone deacetylase inhibitors," Clin Cancer Res, 10(11):3839-3852 (2004).
Piekarz et al., "A Review of Depsipeptide and Other Histone Deacetylase Inhibitors in Clinical Trials," Curr Pharm Des 10:2289-2298 (2004).
Piekarz et al., "Cardiac studies in patients treated with depsipeptide, FK228,1n a phase II trial for T-cell lymphoma," Clin Cancer Res, 12(12):3762-3773 (2006).
Piekarz et al., "Completion of the First Cohort of Patients with Cutaneous T-Cell Lymphoma Enrolled on a Phase II Trial of Depsipeptide ," ASH Annual Meeting Abstracts,106(11):231 (2005).
Piekarz et al., "Epigenetic modifiers: basic understanding and clinical development," Clin Cancer Res, 15(12):3918-3926 (2009).
Piekarz et al , "Inhibitor of histone deactylation, depsipeptide (FR901228), in the treatment of peripheral and cutaneous T-cell lymphoma: a case report," Blood , 98(9):2865-2868 (2001).
Piekarz et al., "Phase II Multi-Institutional Trial of the Histone Deacetylase Inhibitor Romidepsin as Monotherapy for Patients With Cutaneous T-Cell Lymphoma," J Clin Oncol, 27(32):5410-5417 (2009).
Piekarz et al., "Results of a Phase 2 NCI Multicenter Study of Romidepsin in Patients with Relapsed Peripheral T-Cell Lymphoma (PTCL)," ASH Annual Meeting Abstracts 112(11):1567 (2008).
Piekarz et al., "T-cell lymphoma as a model for the use of histone deacetylase inhibitors in cancer therapy: impact of depsipeptide on molecular markers, therapeutic targes, and mechanisms of resistance," Blood , 103(12):4636-4643 (2004).
Piekarz, R., et al, "Update of the NCI multiinstutional phase II trial of romidepsin, FK228,for patients with cutaneous or peripheral T-cell lymphoma,". J Clio Oncol (Meeting Abstracts), 2007.25(18_suppl): p. 8027 (2007).
Prince et al., "Clinical studies of histone deacetylase inhibitors," Clin Cancer Res, 15(12):3958-3969 (2009).
Program of the 4th Japanese Foundation for Cancer Research, International Symposium on Cancer Therapy (ISCC), Feb. 12, 1999.
Rasheed et al., "Histone deacetylase inhibitors in cancer therapy ," Expert Opin Investig Drugs, 16(5):659-678 (2007).
Richon et al., "Histone Deacetylase Inhibitors: A New Class of Potential Therapeutic Agents for Cancer Treatment," Clin Cancer Res 8(3):662-664 (2002).
Richon et al., "Histone deacetylasei inhibitor selectively induces p21WAFI expression and gene-associated histone acetylation,"Proc Natl Acad Sci USA, 97(18):10014-10019 (2000).
Robey et al., "Increased MDRI expression in normal and malignant peripheral blood mononuclear cells obtained from patients receiving depsipetide• (FR901228, FK228, NSC630176)," Clin Cancer Res, 12(5):1547-1555 (2006).
Roychowdhury et al., "Selective efficacy of depsipeptide in a xenograft model of Epstein-Barr virus-positive lymphoproliferative disorder ," J Natl Cancer Inst, 96(19):1447-1457 (2004).
Sakai et al., "MBD3 and HDACI,two components of the NuRDcomplex, are localized at Aurora-A-positive centrosomes in M phase,"J Biol Chem, 277(50):48714-48723 (2002).
Sandor et al., "P21-dependent G arrent with downregulation of cyclin D1 upregulation of cyclin E by the histone deacetylase inhibitor FR901228," Br J Cancer 83(6):817-825, (2000).
Sandor et al., "Phase I trial of the histone deacetylase Inhibitor, depsipeptide (FR901228, NSC 630176), in patients with refractory neoplasms ," Clin Cancer Res, 8(3):718-728 (2002).
Sasakawa et al., "Effects of FK228, a novel histone deacetylase inhibitor, on human lymphoma U-937 cells in vitro and in vivo," Biochem Pharmacol, 64(7):1079-1090 (2002).
Sasakawa et al., "Marker genes to predict sensitivity to FK228, a histone deacetylase inhibitor ," Biochem Pharmacol 69:603 (2005).
Sawa et al., "Anti-tumor effects of Hitone deacetylase inhibitors against human glioma cells," Proc of Japanese Cancer Assoc 60:597 (2001) (w/English translation).
Sawa et al., "Histone deacetylase Inhibitor, FK228, Induces apoptosis and suppresses cell roliferation of human glioblastoma cells in vitro and in vivo ," Acta Neuropathol (Berlin), 07(6):523-531 (2004).
Scala et al., "P-Glycoprotein Substrates and Antagonists Cluster into Two Distinct Groups ," Molecular Pharmacology 51:1024(1997).
Schrump et al., "Clinical and molecular responses in lung cancer patients receiving romidepsin," Clin Cancer Res, 14(1):188-198 (2008).
Schwartsmann et al., "Marine organisms as a source of new anticancer agents," The Lancet Oncology 2(4):221-225 (2001).
Shao et al., "Activity of deacetylase inhibitor panobinostat (LBH589) in cutaneous T-cell lymphoma models: defining molecular mechanisms of resistance," Int. J. Cancer 127:2199(2010).
Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).
Stadler et al., "A phase II study of depsipeptide in refractory metastatic renal cell cancer" Clin Genitourin Cancer, 5(1):57-60 (2006).
Stimson et al., "Biomarkers for predicting clinical responses to HDAC inhibitors," Cancer Letters, 280(2):177-183 (2009).
Su et al., "A phase II study of single agent depsipeptide (DEP) in patients (pts) with radioactive iodine (RAI)-refractory, metastatic,thyroid carcinoma: Preliminary toxicity and efficacy experience," J Clin Oncol (Meeting Abstracts), 24(18 Suppl):5554 (2006).
Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).
Ueda et al., "Action of FR901228, a novel antitumor bicyclic depsipeptide produced by *Chromobacterium violaceum* No. 968, on Ha-ras transformed NIH3T3 cells ," Biosci Biotechnol Biochem, 58(9):1579-1583 (1994).
Ueda et al., "Expression of a full-length cDNA for the human "MDR1" gene confers resistance to colchicines, doxorubicin, and vinblastine," PNAS USA 84:3004 (1987).
Ueda et al., "FR901228, a novel antitumor bicyclic depsipeptide produced by *Chromobacterium violaceum* No. 968. I. Taxonomy,

(56) References Cited

OTHER PUBLICATIONS fermentation, isolation, physico-chemical and biological properties, and antitumor activity," J Antibiot (Tokyo),47:301-310, (1994).

Ueda et al., "FR901228, A Novel Antitumor Bicyclic Depsipeptide Produced by *Chromobacterium violaceum* No. 968," J Antibiot (Tokyo) 47:315-323 (1994).

Vrana et al., "Induction of apoptosis in U937 human leukemia cells by suberoylanilide hydroxamic acid (SAHA) proceeds through pathways that are regulated by Bcl-2/Bcl-XL, c-Jun, and p21CIPI, but independent of p53," Oncogene, 18(50):7016-7025 (1999).

Wang et al., "Fungal metabolite FR901228 inhibits c-Myc Fas ligand expression," Oncogene 17:1503-1508 (1998).

Watanabe et al., "Induction of autophagy in malignant rhabdoid tumor cells by the histone deacetylase inhibitor FK228 through AIF translocation ," Int J Cancer,124(1):55-67 (2009).

Weidle et al. "Inhibition of Histone Deacetylases: a New Strategy to Target Epigentic Modifications for Anticancer Treatment," Anticancer Res 20:1471-1486 (2000).

Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).

Whittaker et al., "Final Results From a Multicenter, International, Pivotal Study of Romidepsin in Refractory Cutaneous T-Cell Lymphoma," J Clin Oncol 28:4485-4491 (2010).

Whittaker et al., "international multicenter phaSe II study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).

Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276 (2005).

Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).

Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).

Non final office action for U.S. Appl. No. 12/298,436 dated Jun. 8, 2011.

Final office action for U.S. Appl. No. 12/298,436 dated Feb. 1, 2012.

Non final office action for U.S. Appl. No. 13/229,581 dated Jul. 12, 2013.

Non final office action for U.S. Appl. No. 13/627,848 dated Oct. 17, 2013.

Final office action for dated U.S. Appl. No. 13/627,848 Apr. 2, 2014.

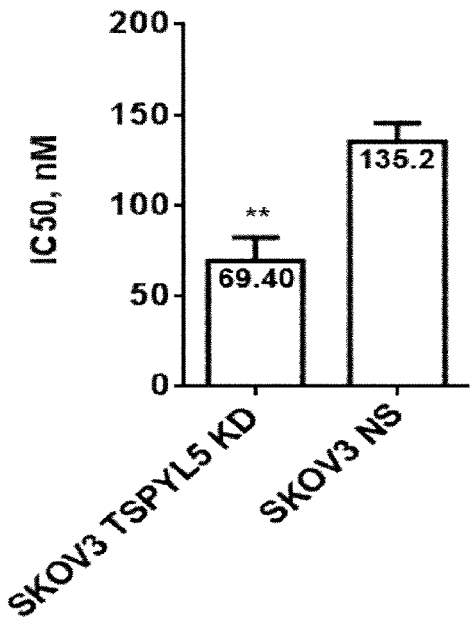
Figure 5A
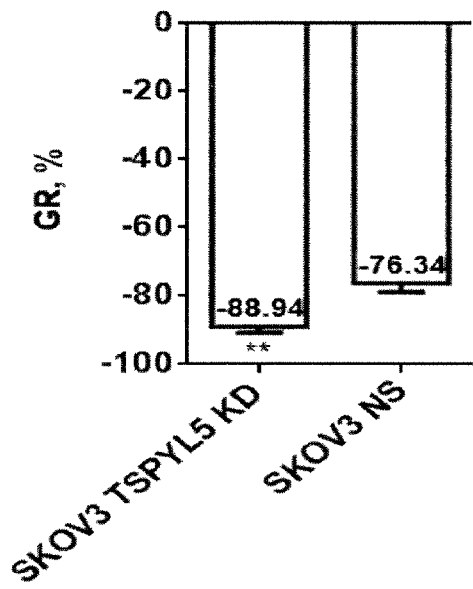
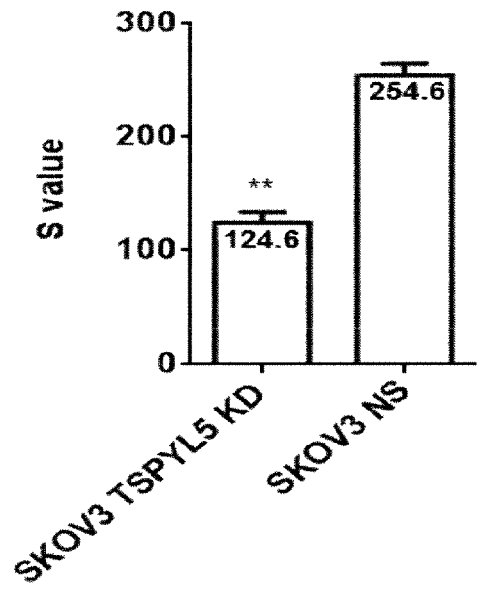
Figure 5B
Figure 5C

| Compound | Chemical Class | HDAC Ki (nm) | | | | | | | | |
|---|---|---|---|---|---|---|---|---|---|---|
| | | 1 | 2 | 3 | 4 | 5 | 6 | 7 | 8 | 9 |
| Romidepsin | cyclic peptide | 0.002 | 0.038 | 0.150 | 21 | 550 | 9.500 | 1250 | 0.1500 | 1100 |
| Panobinostat | hydroxamic acid | 1.000 | 0.650 | 1.100 | 550 | 80 | 1.500 | 4550 | 105 | 3200 |
| SAHA (Vorinostat) | hydroxamic acid | 1.300 | 1.600 | 5.000 | NI | 3600 | 1.600 | NI | 480 | NI |
| MS-275 (Entinostat) | benzamide | 22 | 65 | 35 | NI | NI | NI | NI | NI | NI |
| | | Relative Activities (to HDAC 1) | | | | | | | | |
| Romidepsin | cyclic peptide | 1.0 | 25.3 | 100 | 14000 | 366667 | 6333 | 833333 | 100 | 733333 |
| Panobinostat | hydroxamic acid | 1.0 | 0.7 | 1.1 | 550 | 80 | 1.5 | 4550 | 105 | 3200 |
| SAHA (Vorinostat) | hydroxamic acid | 1.0 | 1.2 | 3.8 | NI | 2769 | 1.2 | NI | 369 | NI |
| MS-275 (Entinostat) | benzamide | 1.0 | 3.0 | 1.6 | NI | NI | NI | NI | NI | NI |

Figure 6

RESISTANCE BIOMARKERS FOR HDAC INHIBITORS

RELATED APPLICATIONS

This application claims priority to U.S. provisional application Ser. No. 61/698,341, filed Sep. 7, 2012; U.S. provisional application Ser. No. 61/726,464, filed Nov. 14, 2012; and U.S. provisional application Ser. No. 61/784,501, filed Mar. 14, 2013, which are incorporated herein by reference in their entireties.

The invention relates generally to the field of personalized medicine and, more specifically to the discovery that TSPYL5, encoding testis-specific Y-like protein, serves as a tumor biomarker for resistance to cancer treatment with a histone deacetylase (HDAC) inhibitor.

BACKGROUND

Cancer is a major public health problem in the United States and in the world. Currently, one in 4 deaths in the United States is due to cancer. Each year, the American Cancer Society estimates the numbers of new cancer cases and deaths expected in the United States in the current year and compiles the most recent data on cancer incidence, mortality, and survival based on incidence data from the National Cancer Institute, the Centers for Disease Control and Prevention, and the North American Association of Central Cancer Registries and mortality data from the National Center for Health Statistics. A total of 1,596,670 new cancer cases and 571,950 deaths from cancer were projected to occur in the United States in 2011. Aging of the general population and development of new forms of cancer contribute to the problem.

Attempts have been made to identify genes or other markers that would either predict response to treatment, or correlate with response to treatment. In 2009, the laboratory of Nicholas B. La Thangue published the results of a genome-wide loss of function screen that identified a role for HR23B as a sensitivity determinant for HDAC inhibitor that induced apoptosis in cells (Fotheringham et al., *Cancer Cell* 15:57 (2009). In a subsequent paper, the authors noted a frequent coincidence between HR23B expression and clinical response to HDAC inhibition (Khan et al., *PNAS* 107:6532 (2010).

Other studies described markers that correlate with sensitivity to HDAC inhibitors in cells. Shao et al. (*Int. J. Cancer* 127:2199(2010)) compared 4 lines that are either sensitive or resistant to panobinostat treatment and found that inhibition of BCL2 sensitized resistant lines to panobinostat treatment. BCL2 blocks the pro-apoptotic activity of BAX, and knockdown of BAX was found to diminish sensitivity to panobinostat treatment. These results were in line with previous studies showing that overexpression of BCL2 and BCL-xl blocked HDAC inhibitor mediated apoptosis (Bolden et al., *Nature Reviews Drug Discovery* 5:769 (2006), including apoptosis mediated by romidepsin (Peart et al., *Cancer Research* 63:4460 (2003). Later studies showed that romidepsin is able to induce apoptosis in lymphomas overexpressing BCL2 with delayed kinetics, but not in cells overexpressing BCL-xl (Newbold et al, *Mol. Cancer Ther.* 7:1066 (2008); WO/2010/047714). Peart et al. confirmed romidepsin as a substrate for P-glycoprotein (P-gp), and showed that cells overexpressing P-gp are resistant to apoptosis induced by the drug. Also Scala showed romidepsin to be a P-gp substrate (Scala et al., *Molecular Pharmacology* 51:1024(1997) and a substrate for Multidrug Resistance Associated Protein 1 (MRP1), but the major mechanism of acquired resistance to romidepsin in cells appears to be up-regulation of P-gp (Xiao et al., *J Pharmacol and Exp Ther* 313:268(2005)). In spite of the correlation between P-gp expression and romidepsin sensitivity that is observed in cell culture assays, no association exists between P-gp expression and clinical response (Bates et al., *Br J Haematol* 148:256 (2010).

Various laboratories have tried to establish gene expression signatures that correlate with response to treatment to HDAC inhibitors (Stimson et al., *Cancer Lett* 280:177 (2009)). However, these signatures vary from study to study and are most likely unique to the tumor type studied and the HDAC inhibitor used. For example, Yuka Sasakawa and colleagues tried to identify markers that predict sensitivity to romidepsin (Sasakawa et al., *Biochem Pharmacol* 69:603 (2005)). This study compared expression profiles of sensitive and resistant to romidepsin tumors and identified caspase 9 and MKP-1 genes as marker genes to predict sensitivity to romidpsin treatment. However, the validity of these markers is likely to be limited to these specific studies.

Between 2,000 and 3,000 new cases of cutaneous T-cell lymphoma (CTCL) occur in the United States each year, with mycosis fungoides (MF) and the Sézary syndrome (SS) being the predominant subtypes. Romidepsin activity in T-cell lymphomas was observed in phase I and II trials conducted by the National Cancer Institute (NCI) in patients with both MF and SS. (Piekarz et al., *Blood* 103: 4636 (2004); Sandor et al., *Clin Cancer Res* 8:718 (2002); Marshall et al., J Exp Ther Oncol 2:325 (2002); Piekarz et al., *Blood* 98:2865 (2001); Piekarz et al., *J. Clinical Oncology* 27 (32):5410 (2009)). Romidepsin was shown in a phase II clinical trial to have single-agent clinical activity with significant and durable responses in patients with cutaneous T-cell lymphoma (CTCL) (Piekarz et al., *J Clinical Oncology* 27 (32):5410 (2009)). Romidepsin has also been shown to have significant and sustainable single-agent activity and an acceptable safety profile for treatment of refractory CTCL (Whittaker et al. *J Clin Oncol* 28:4485-4491 (2010)).

Little is known about TSPYL5, which encodes Testis-specificY-encoded-like protein 5. It contains a nucleasome assembly protein domain (NAP-domain) that acts as histone chaperone. TSPYL5 has been shown to be involved in cell growth and resistance to radiation in A549 cells (Kim et al., *Biochem and Biophys Res Comm* 392:448 (2010). It is a target of epigenetic silencing in gastric cancers (Jung et al., *Lab Invest* 88:153(2008), and glioma (Kim et al., *Cancer Res* 66:7490 (2006)) and is thought to mediate some of its function by suppressing p53 activity via physical interaction with USP7 (Epping et al., *Nature Cell Biol* 13:102 (2011). There is no known connection between the levels of TSPYL5 and sensitivity to treatment with romidepsin or other HDAC inhibitors.

Currently, patients receiving treatment with romidepsin are not selected for treatment based on the expression of predictive markers. To improve clinical outcomes, a need exists to identify biomarkers that allow selecting cancer patients that are more likely to respond positively to HDAC inhibitor therapy while deselecting cancer patients that are likely to be resistant to HDAC inhibitor therapy.

SUMMARY

In one aspect of the invention, a method is provided for identifying a cancer patient at risk for resistance to an HDAC inhibitor therapy, comprising obtaining a tumor sample from the cancer patient; detecting the presence of Testis-specific Y-encoded-like protein 5 (TSPYL5) expression in the sample; quantifying a level of the TSPYL5 expression in the sample, wherein a high level of the TSPYL5 expression, relative to a defined expression threshold of the TSPYL5, correlates with resistance to the HDAC inhibitor therapy; and applying the correlation to identify the cancer patient at risk for resistance to the HDAC inhibitor therapy.

Also provided is a method for identifying a cancer patient with an increased likelihood of a positive clinical response to an HDAC inhibitor therapy comprising obtaining a tumor sample from the cancer patient; detecting the presence of Testis-specific Y-encoded-like protein 5 (TSPYL5) expression in said sample; quantifying a level of said TSPYL5 expression in said sample, wherein a low level of the TSPYL5 expression, relative to a defined expression threshold of the TSPYL5, identifies said cancer patient with an increased likelihood of a positive clinical response to said HDAC inhibitor therapy.

In some embodiments, the methods provided herein further comprise communicating the identification of the cancer patient to a health care provider. In additional embodiments, the communication to a health care provider informs a subsequent treatment selection for the cancer patient. In certain embodiments the treatment selection involves either selecting or deselecting the cancer patient for HDAC inhibitor therapy.

In additional embodiments, the methods provided herein further comprise administering a therapeutically effective amount of the HDAC inhibitor to the selected patient. In further embodiments, the HDAC inhibitor is selected from the group consisting of romidepsin, panobinostat, vorinostat and entinostat. In a particular embodiment, the HDAC inhibitor is romidepsin.

In further embodiments, the methods provided herein further comprise initiating HDAC inhibitor therapy. In further embodiments, the HDAC inhibitor therapy comprises an HDAC inhibitor selected from the group consisting of romidepsin, panobinostat, vorinostat and entinostat. In a particular embodiment, the HDAC inhibitor is romidepsin.

Also provided are embodiments where the HDAC inhibitor is selected from the group consisting of romidepsin, panobinostat, vorinostat and entinostat. In certain embodiments, the HDAC inhibitor is romidepsin.

In yet further embodiments, the level of the TSPYL5 expression is determined by measuring the amount of TSPYL5 protein using an immunoassay, for example, an immune-polymerase chain reaction (immuno-PCR).

Also provided are kits comprising a container filled with an HDAC inhibitor, reagents for determining the level of the TSPYL5 gene or protein in a tumor sample, and instructions for determining the level of expression of TSPYL5 gene or protein in a tumor sample of a patient having cancer.

The present embodiments can be understood more fully by reference to the detailed description and examples, which are intended to exemplify non-limiting embodiments.

DESCRIPTION OF THE DRAWINGS

FIG. 5 depicts the effect of knockdown of TSPYL5 expression on sensitivity of SKOV-3 cells to romidepsin using shRNA, as measured by the effect of romidepsin treatment on $IC_{50}$ (Panel A), growth rate (GR) (Panel B) and S value (Panel C). Sensitivity of TSPYL5 knockdown cells to romidepsin is increased as measured by $IC_{50}$, S value and growth inhibition. SKOV3 cells expressing either TSPYL5 shRNA (SKOV3 TSPYL5 KD) or non-silencing control shRNA (SKOV3 NS) were created using lentiviral infection. Knockdown of TSPYL5 in SKOV3 TSPYL5 KD cells was verified using western blot (data not shown) and quantitative PCR. Expression of TSPYL5 in these cells was reduced by 70% (data not shown) After selection of stable pools with puromycen, cells were treated with varying concentrations of romidepsin for determination of $IC_{50}$, GI and S value. The data shown are means and standard deviations from 5 independent experiments. Panel A: Romidepsin $IC_{50}$s for SKOV3 TSPYL5 KD cells and SKOV3 NS cells. Panel B: Romidepsin GI for SKOV3 TSPYL5 KD cells and SKOV3 NS cells. Panel C: Romidepsin S value for SKOV3 TSPYL5 KD cells and SKOV3 NS cells. Numbers in white are means obtained from 5 experiments. The asterisks describe values levels of statistical significance, with 2 asterisks depicting p-values between 0.01 and 0.001.

FIG. 6 provides a table comparing the inhibitory activity for Histone Deacetylases 1 through 9 of 4 commonly used HDAC inhibitors. HDACs 1, 2, 3 and 8) are known as class 1 HDACs, while HDACs 4, 5, 6, 7 and 9 are known as class 2 HDACs. The table shows Ki in nM, and relative activities compared to HDAC1 (NI: no inhibition). All 4 HDAC inhibitors inhibit the class 1 HDACs 1 and 2. MS-275 and romidepsin are more selective than the hydroxamic acids panobinostat and SAHA, which inhibit the class 2 HDAC 6 in addition to inhibiting class 1 HDACs 1, 2 and 3, and, to a lesser degree, HDAC 8. Based on data from Bradner et al., *Nat Chem Biol* 6:238 (2010).

DETAILED DESCRIPTION

Definitions

Figure 1:
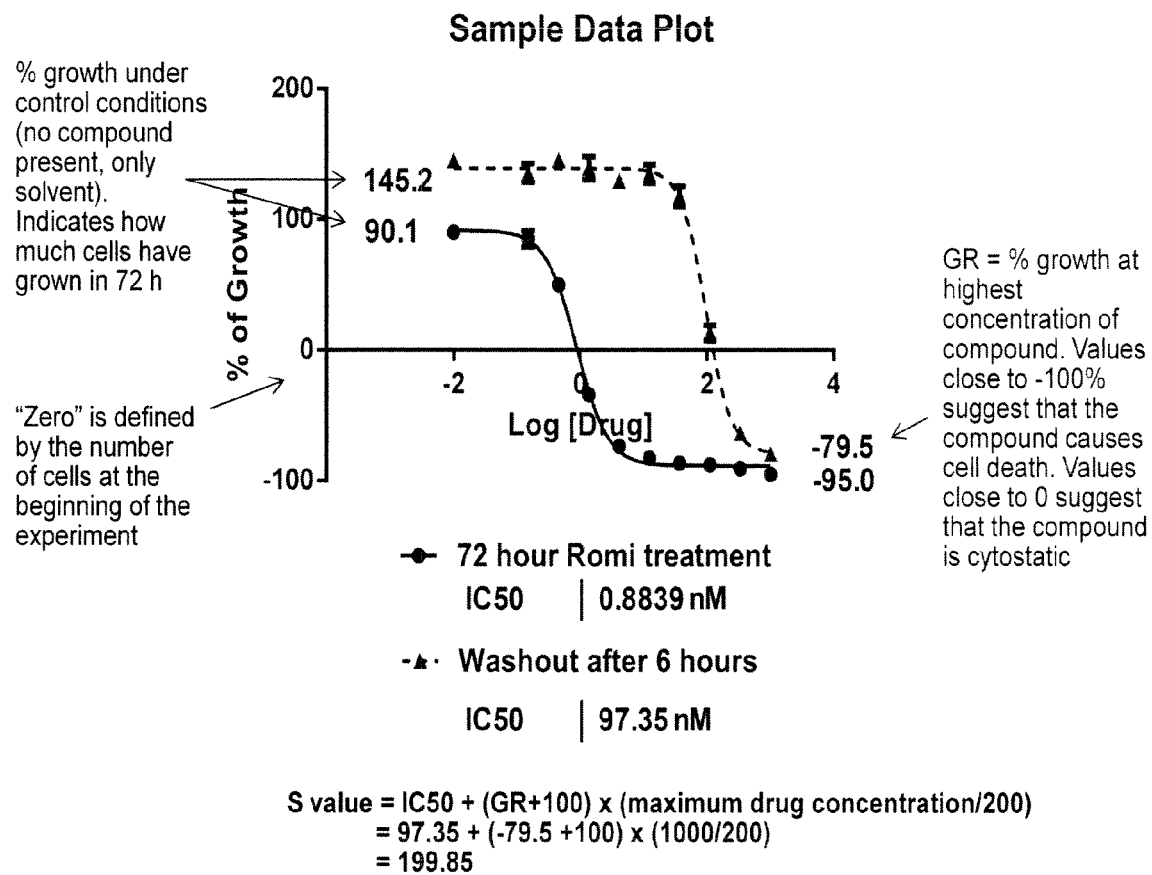
FIG. 1 depicts a sample data plot showing cell growth at various concentrations of romidepsin after 6 h and 72 h drug treatment. Percent growth is plotted against drug concentration. Cell growth for both treatments was measured after 72 h using CellTiter-Glo®. Measurements were normalised to numbers of cells at the beginning of the experiment (d0) as measured by CellTiter-Glo®.

As used in the specification and the accompanying claims, the indefinite articles "a" and "an" and the definite article "the" include plural as well as singular referents, unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the term "HDAC inhibitor therapy" refers to the administration of an HDAC inhibitor to a patient in order to effect the treatment, eradication or amelioration of a condition, disorder, or disease, or of one or more symptoms associated with the a condition, disorder, or disease. In certain embodiments, the administration can be aimed to minimize the spread or worsening of the disease or disorder resulting from the administration of the HDAC inhibitor to a subject with such a disease or disorder. In some embodiments, the term refers to the administration of a compound or dosage form provided herein, with or without one or more additional active agent(s), after the diagnosis or the onset of symptoms of the disease. In some embodiments, the term may encompass prevention.

As used herein, and unless otherwise specified, the term "therapeutically effective amount" in connection with the HDAC inhibitor refers to that amount of the compound being administered sufficient to slow the development of or alleviate to some extent one or more of the symptoms of the condition or disorder being treated, for example cancer, or slowing or halting further progression or worsening of those symptoms, in a subject at risk for cancer. The effective amount of the HDAC inhibitor, for example in a pharmaceutical composition, may be at a level that will exercise the desired effect; for example, about $0.005\text{ mg/m}^2$ to $100\text{ mg/m}^2$, about $0.05\text{ mg/m}^2$ to $90\text{ mg/m}^2$, about $0.5\text{ mg/m}^2$ to $80\text{ mg/m}^2$, about $1.0\text{ mg/m}^2$ to $70\text{ mg/m}^2$, about $2.0\text{ mg/m}^2$ to $60\text{ mg/m}^2$, about $3.0\text{ mg/m}^2$ to $50\text{ mg/m}^2$, about $4.0\text{ mg/m}^2$ to $40\text{ mg/m}^2$, about $5.0\text{ mg/m}^2$ to $30\text{ mg/m}^2$, about $10.0\text{ mg/m}^2$ to $20\text{ mg/m}^2$, about $11.0\text{ mg/m}^2$ to $19\text{ mg/m}^2$, about $12.0\text{ mg/m}^2$ to $18.0\text{ mg/m}^2$, about $13.0\text{ mg/m}^2$ to $17.0\text{ mg/m}^2$, about $14.0\text{ mg/m}^2$ to $16.0\text{ mg/m}^2$, about $14.5\text{ mg/m}^2$ to $15.5\text{ mg/m}^2$, about $14.6\text{ mg/m}^2$ to $15.4\text{ mg/m}^2$, about $14.7\text{ mg/m}^2$ to $15.3\text{ mg/m}^2$, about $14.8\text{ mg/m}^2$ to $15.2\text{ mg/m}^2$ of a subject's body weight, in unit dosage for both oral and parenteral administration. As will be apparent to those skilled in the art, it is to be expected that the effective amount of an HDAC inhibitor disclosed herein may vary depending on the severity of the indication being treated.

A "biological marker" or "biomarker" is a substance, the change and/or the detection of which indicates a particular biological state, such as, for example, the resistance of a disease, for example, cancer, to a given treatment, for example, HDAC inhibitor therapy.

An "increased likelihood" in reference to a positive clinical response is intended to mean that a cancer patient has a higher likelihood to respond to HDAC inhibitor therapy compared to the average likelihood of responsiveness to HDAC inhibitor therapy calculated from a random pool of cancer patients.

The term "responsiveness" or "responsive" when used in reference to a treatment refer to the degree of effectiveness of the treatment in lessening or decreasing the symptoms of a disease, e.g., cancer.

The term "positive clinical response" when used in reference to a HDAC inhibitor therapy refers to a lessening or decrease of one or more of the symptoms of the disease treated.

The term "expressed" or "expression" refers to the transcription from a gene to produce an RNA nucleic acid molecule, e.g., mRNA, at least complementary in part to a region of one of the two nucleic acid strands of the gene. The term "expressed" or "expression" as used herein also refers to the translation from an RNA molecule to give a protein, a polypeptide, or a portion thereof.

The terms "expression threshold," and "defined expression threshold" are used interchangeably and refer to the level of a gene or protein above which the gene or gene product serves as a predictive marker for patient resistance to HDAC inhibitor therapy. The expression threshold is a relative level and is established by quantifying the expression of TSPYL5 in the tumor cells of a number of patients with similar tumors. The expression level of TSPYL5 found in the tumor cells of the patients with the lowest expression level is defined as the expression threshold. Patients are considered likely to respond to treatment with an HDAC inhibitor if their tumor has expression levels close to that threshold, while patients are considered likely to be resistant to treatment with an HDAC inhibitor if their tumor has expression levels higher than that threshold. The threshold can be defined experimentally from clinical studies. The expression threshold can be selected either for maximum sensitivity, or for maximum selectivity, or for minimum error. The determination of the expression threshold is well within the knowledge of those skilled in the art.

A "low" level of TSPYL5 expression is a level of expression at or below a predetermined expression threshold. A "high" level of a TSPYL5 expression is a level of TSPYL5 gene expression above a predetermined expression threshold.

It is understood that the genes and/or proteins described herein are inclusive of allelic variant isoforms, synthetic nucleic acids and/or proteins, nucleic acid and/or proteins isolated from tissue and cells, and modified forms thereof. It is also understood that the genes and/or proteins described herein are also known to exist in various forms, including variants and mutants, and are contemplated herein. The genes and/or proteins described herein further include nucleic acid sequences and/or amino acid sequences having at least 65% identity with the gene or protein to be detected and are included within embodiments described herein.

A used herein, the term "subject" or "patient" refers generally to a mammal. In particular embodiments, the term refers to a cancer patient that has been diagnosed as having cancer.

As used herein, and unless otherwise specified, the term "unit dose" when used in reference to a therapeutic composition refers to physically discrete units suitable as unitary dosage for humans, each unit containing a predetermined quantity of active material calculated to produce the desired therapeutic effect in association with the required diluents or excipients, i.e., carrier, or vehicle.

The term "tumor," as used herein, refers to all neoplastic cell growth and proliferation, whether malignant or benign, and all pre-cancerous and cancerous cells and tissues. The term "tumor sample" refers to a biological sample useful for detection of TSPYL5 comprising tumor cells and includes, without limitation, biopsies, tissues, blood, cells, secretions, cerebrospinal fluid, bile, lymph fluid, urine and faeces, or tissue which has been removed from organs, such as, for example, breast, lung, intestine, skin, cervix, prostate, and stomach. For example, a tumor sample can comprise a region of functionally related cells or adjacent cells as well as circulating tumor cells isolated from blood. In one example, a tumor sample includes blood obtained from a cancer patient, such as whole blood or serum.

As used herein, and unless otherwise specified, the term "biological sample," generally refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a serum sample, a urine sample, a skin sample, and the like. Preferred biological samples include but are not limited to whole blood, partially purified blood, PBMCs, tissue biopsies, and the like.

As used herein, and unless otherwise specified, the terms "cancer" and "cancerous" refer to or describe a group of diseases which are characterized by uncontrolled growth and spread of abnormal cells. Cancers include, but are not limited to, carcinomas, sarcomas, leukemias, lymphomas and the like. In certain embodiments, cancer is a hematological malignancy. In certain embodiments, cancer is a solid tumor.

In certain embodiments the present disclosure relates to treatment of hematological malignancies. Manifestations of hematological malignancies include circulating malignant cells and malignant masses. Hematological malignancies are types of cancers that affect the blood, bone marrow, and/or lymph nodes. Hematological malignancies that may be treated using romidepsin include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), multiple myeloma, and myelodysplastic syndromes. In certain embodiments, romidepsin is used to treat multiple myeloma. In certain particular embodiments, the cancer is relapsed and/or refractory multiple myeloma. In other embodiments, romidepsin is used to treat chromic lymphocytic leukemia (CLL). In certain particular embodiments, the cancer is relapsed and/or refractory CLL. In other embodiments, romidepsin is used to treat chromic myelogenous leukemia (CML). In certain embodiments, romidepsin is used to treat acute lymphoblastic leukemia (ALL). In certain embodiments, romidepsin is used to treat acute myelogenous leukemia (AML). In certain embodiments, the cancer is cutaneous T-cell lymphoma (CTCL). In other embodiments, the cancer is peripheral T-cell lymphoma (PTCL). In certain embodiments, the cancer is a myelodysplastic syndrome.

In some embodiments of the present disclosure, cancers treated include, but are not limited to, leukemias and lymphomas such as cutaneous T-cell lymphoma (CTCL), peripheral T-cell lymphoma, lymphomas associated with human T-cell lymphotropic virus (HTLV) such as adult T-cell leukemia/lymphoma (ATLL), B-cell lymphomas, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndromes.

In some such embodiments the disclosure relates to treatment of solid tumors such as lung, breast, colon, liver, pancreas, renal, prostate, ovarian, and/or brain. In some embodiments, the disclosure relates to treatment of pancreatic cancer. In some embodiments, the disclosure relates to treatment of renal cancer. In some embodiments, the disclosure relates to treatment of prostate cancer. In some embodiments, the disclosure relates to treatment of sarcomas. In some embodiments, the disclosure relates to treatment of soft tissue sarcomas.

In some embodiments, cancers that can be treated are solid cancers that includes, but are not limited to, mesothelioma, common solid tumors of adults such as head and neck cancers (e.g., oral, laryngeal and esophageal), genitourinary cancers (e.g., prostate, bladder, renal, uterine, ovarian, testicular, rectal and colon), melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.). In certain embodiments, the cancer is melanoma. In other embodiments, the cancer is gastric cancer. In some embodiments, the disclosure relates to treatment of solid tumors.

Cancers that may be treated using the methods provided herein, including combination therapy, include but not limited to, colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, and neuroendocrine cancer.

In certain embodiments, cancer is pancreatic cancer. In certain embodiments, cancer is prostate cancer. In certain specific embodiments, the prostate cancer is hormone refractory prostate cancer.

In some particular embodiments, provided are methods to treat leukemias. In some embodiments, leukemia is chronic lymphocytic leukemia, chronic myelogenous leukemia, acute lymphocytic leukemia, acute myelogenous leukemia, or adult T cell leukemia/lymphoma.

In some embodiments, provided are methods of treating lymphomas. In some embodiments, lymphoma is Hodgkin's or non-Hodgkin's (e.g., T-cell lymphomas such as peripheral T-cell lymphoma, cutaneous T-cell lymphoma, etc.) lymphoma.

In some embodiments, the disclosure relates to the treatment of multiple myeloma and/or myelodysplastic syndromes.

As used herein, and unless otherwise specified, the term "resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "histone deacetylase inhibitor" or "HDAC inhibitor" refers to a compound that modulates protein acetylation by blocking zinc-dependent histone deacetylases involved in removing acetyl groups from lysine residues. HDAC inhibitors can be separated into several structurally distinct classes: short-chain fatty acids (i.e., valproic acid), hydroxamic acids (i.e., vorinostat, TSA, tubacin, and PCI-24781), benzamides (i.e., entinostat), cyclic tetrapeptides (i.e., romidepsin), and electrophilic ketones. For example, the HDAC inhibitors romidepsin, panobinostat, vorinostat (SAHA) and entinostat (MS-275) inhibit the class 1 HDACs 1 and 2. Entinostat and romidepsin are more selective than the hydroxamic acids panobinostat and SAHA, which inhibit the class 2 HDAC 6 in addition to inhibiting class 1 HDACs 1, 2 and 3, and, to a lesser degree, HDAC 8. Based on data from Bradner et al., *Nat Chem Biol* 6:238 (2010).

As used herein, and unless otherwise specified, the terms "determining," "measuring," "evaluating," "assessing," and "assaying," generally refer to any form of measurement, and include determining if an element is present or not. These terms include both quantitative and/or qualitative determinations. Assessing may be relative or absolute. The phrase "assessing the presence of" can include determining the amount of something present, as well as determining whether it is present or absent.

As used herein, and unless otherwise specified, the phrase "assessing the activity of an agent," encompasses the assessment of the "presence" of the treatment by the agent, e.g., whether the patient has been treated by or administered the agent compound. The phrase also encompasses the assessment of the "extent" of the treatment, e.g., doses and length of treatment determined in quantitative terms. The phrase also encompasses assessing the effect of the agent, e.g., response or results of the treatment.

As used herein, and unless otherwise specified, the terms "isolated" and "purified" generally describes a composition of matter that has been removed from its native environment (e.g., the natural environment if it is naturally occurring), and thus is altered by the hand of man from its natural state. An isolated protein or nucleic acid is distinct from the way it exists in nature.

The term "polypeptide," "protein," or "peptide," as used herein interchangeably, refers to a polymer of two or more amino acids in a serial array, linked through one or more peptide bond(s). The term encompasses proteins, protein fragments, protein analogues, oligopeptides, peptides, and peptide mimics. The amino acids of a polypeptide, protein, or peptide can be naturally occurring amino acids or synthetic amino acids (e.g., mimics of naturally occurring amino acids). A polypeptide, protein, or peptide can be made synthetically or purified from a biological sample. The term also encompasses modified polypeptides, proteins, and peptides, e.g., a depsipeptide, glycopolypeptide, glycoprotein, or glycopeptide; or a lipopolypeptide, lipoprotein, or lipopeptide.

The term "antibody" refers to a polypeptide that specifically binds an epitope (e.g., an antigen). The term "antibody" is used herein in the broadest sense and covers fully assembled antibodies, antibody fragments which retain the ability to specifically bind to an antigen (e.g., Fab, F(ab')$_2$, Fv, and other fragments), single chain antibodies, diabodies, antibody chimeras, hybrid antibodies, bispecific antibodies, and humanized antibodies. The term "antibody" also covers both polyclonal and monoclonal antibodies.

As used herein, and unless otherwise specified, the term "label" or a "detectable moiety" in reference to a protein, generally refers to a composition that, when linked with a protein, renders the protein detectable, for example, by spectroscopic, photochemical, biochemical, immunochemical, or chemical means. Exemplary labels include but are not limited to radioactive isotopes, magnetic beads, metallic beads, colloidal particles, fluorescent dyes, enzymes, biotin, digoxigenin, haptens, and the like. A "labeled protein or oligopolypeptide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the protein or probe can be detected by detecting the presence of the label bound to the protein or probe.

The term "probe" as used herein, refers to a capture agent, for example, a nucleic acid sequence, that is directed to a specific target DNA or mRNA biomarker sequence. Accordingly, each probe of a probe set has a respective target DNA or mRNA biomarker. A probe/target DNA or mRNA duplex is a structure formed by hybridizing a probe to its target DNA or mRNA biomarker.

The term "nucleic acid probe" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not substantially interfere with hybridization. It will be understood by one of skill in the art that a probe may bind a target sequence lacking complete complementarity with the probe sequence depending upon the stringency of the hybridization conditions. The probes are preferably directly labeled with, for example, isotopes, chromophores, lumiphores, or chromogens, or indirectly labeled with biotin to which a streptavidin complex may later bind. By assaying for the presence or absence of the probe, one can detect the presence or absence of a target DNA or mRNA biomarker of interest.

The term "stringent assay conditions" refers to conditions that are compatible to produce binding pairs of nucleic acids, e.g., probes and target DNA or mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

As used herein, and unless otherwise specified, the term "pharmaceutically acceptable" refers to molecular entities and compositions that are physiologically tolerable and do not typically produce an allergic or similar untoward reaction, such as gastric upset, dizziness and the like, when administered to a human.

As used herein, and unless otherwise specified, the term "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier must be "acceptable" in the sense of being compatible with the other ingredients of the formulation and not injurious to a subject to whom it is administered. Nor should an acceptable carrier alter the specific activity of the subject compounds.

As used herein, and unless otherwise specified, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

The term "prodrug" means a derivative of a compound that can hydrolyze, oxidize, or otherwise react under biological conditions (in vitro or in vivo) to provide the compound. Examples of prodrugs include, but are not limited to, derivatives of romidepsin, its reduced, oxidized, and oligomerized forms. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, New York 1985).

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning; A Laboratory Manual* (2d ed.), 1989; Glover, ed. *DNA Cloning*, Volumes I and II, 1985; Gait, ed., *Oligonucleotide Synthesis,* 1984; Hames & Higgins, eds. *Nucleic Acid Hybridization*, 1984; Hames &. Higgins, eds., *Transcription and Translation*, 1984; Freshney, ed., *Animal Cell Culture*, 1986; *Immobilized Cells and Enzymes*, IRL Press, 1986; *Immunochemical Methods in Cell and Molecular Biology* (Academic Press, London); Scopes, *Protein Purification: Principles and Practice* (2d ed.; Springer Verlag, N.Y.), 1987; and Weir and Blackwell, eds. *Handbook of Experimental Immunology*, Volumes I-IV, 1986.

Romidepsin

Romidepsin is a natural product which was isolated from *Chromobacterium violaceum* by Fujisawa Pharmaceuticals (Published Japanese Patent Application Hei 7 (1995)-64872; and U.S. Pat. No. 4,977,138, issued Dec. 11, 1990, each of which is incorporated herein by reference). Various preparations and purifications of romidepsin are described in PCT Publication WO 2002/20817, which is incorporated herein by reference. Solid forms of romidpesin are described in U.S. Pat. Nos. 7,608,280 and 7,611,724, a method of manufacturing romidepsin is described in US 2010/0093610 and US 2009/0209616, and a romidpesin formulation is described in US2012/0046442, and each of the aformentioned is incorporated herein by reference in its entirety.

Romidepsin is a bicyclic depsipeptide consisting of four amino acid residues (D-valine, D-cysteine, dehydrobutyrine, and L-valine) and a novel acid (3-hydroxy-7-mercapto-4-heptenoic acid), which contains both amide and ester bonds. Romidepsin can be obtained from *C. violaceum* using fermentation. It can also be prepared by synthetic or semi-synthetic means. The total synthesis of romidepsin reported by Kahn et al. (*J. Am. Chem. Soc.* 118:7237-7238, 1996) involves 14 steps and yields romidepsin in 18% overall yield. The structure of romidepsin is shown below (formula I):

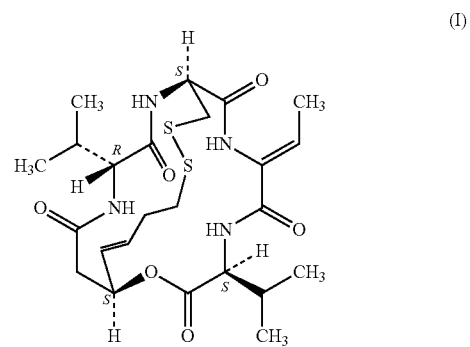

Romidepsin has been shown to have antimicrobial, immunosuppressive, and anti-tumor activities. Romidepsin is sold under the tradename Istodax® and is approved in the United States for the treatment of cutaneous T-cell lymphoma (CTCL) in patients who have received at least one prior systemic therapy, and for the treatment of peripheral T-cell lymphoma (PTCL) in patients who have received at least one prior therapy. It is was tested for multiple myeloma and solid tumors (e.g., prostate cancer, pancreatic cancer, etc.) and is thought to act by selectively inhibiting deacetylases (e.g., histone deacetylase, tubulin deacetylase) (Nakajima et al., *Exp Cell Res* 241:126-133, 1998). One mode of action of romidepsin involves the inhibition of one or more classes of histone deacetylases (HDAC).

Exemplary forms of romidepsin include, but are not limited to, salts, esters, pro-drugs, isomers, stereoisomers (e.g., enantiomers, diastereomers), tautomers, protected forms, reduced forms, oxidized forms, derivatives, and combinations thereof, with the desired activity (e.g., deacetylase inhibitory activity, aggressive inhibition, cytotoxicity). In certain embodiments, romidepsin is a pharmaceutical grade material and meets the standards of the U.S. Pharmacopoeia, Japanese Pharmacopoeia, or European Pharmacopoeia. In certain embodiments, the romidepsin is at least 95%, at least 98%, at least 99%, at least 99.9%, or at least 99.95% pure. In certain embodiments, the romidepsin is at least 95%, at least 98%, at least 99%, at least 99.9%, or at least 99.95% monomeric. In certain embodiments, no impurities are detectable in the romidepsin materials (e.g., oxidized material, reduced material, dimerized or oligomerized material, side products, etc.). Romidepsin typically includes less than 1.0%, less than 0.5%, less than 0.2%, or less than 0.1% of total other unknowns. The purity of romidepsin may be assessed by appearance, HPLC, specific rotation, NMR spectroscopy, IR spectroscopy, UV/Visible spectroscopy, powder x-ray diffraction (XRPD) analysis, elemental analysis, LC-mass spectroscopy, or mass spectroscopy.

In one embodiment, romidepsin is present in a derivative form.

In one embodiment, the derivative of romidepsin is of the formula (II):

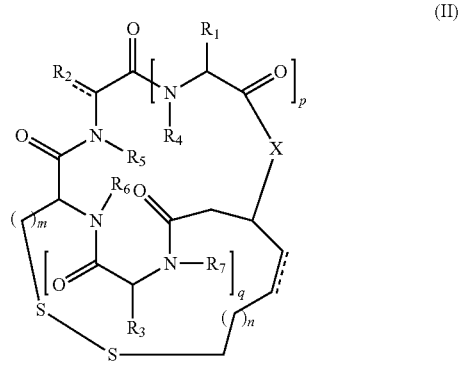

(II)

wherein
n is 1, 2, 3 or 4;
n is 0, 1, 2 or 3;
p and q are independently 1 or 2;
X is O, NH, or $NR_8$;
$R_1$, $R_2$, and $R_3$ are independently hydrogen, unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl; and $R_4$, $R_5$, $R_6$, $R_7$ and $R_8$ are independently hydrogen, or substituted or unsubstituted, branched or unbranched, cyclic or acyclic aliphatic; and pharmaceutically acceptable forms thereof.

In one embodiment, m is 1, n is 1, p is 1, q is 1, X is O, $R_1$, $R_2$, and $R_3$ are unsubstituted or substituted, branched or unbranched acyclic aliphatic. In one embodiment, $R_4$, $R_5$, $R_6$ and $R_7$ are all hydrogen one embodiment, the derivative of romidepsin is of the formula (III):

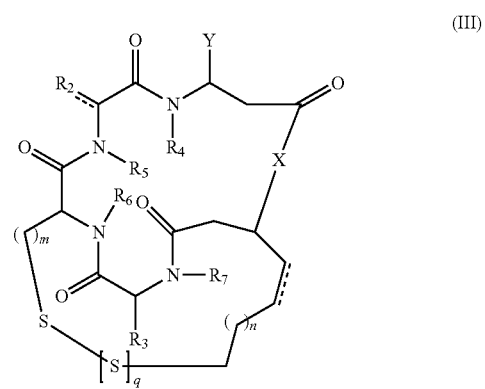

(III)

wherein:
m is 1, 2, 3 or 4;
n is 0, 1, 2 or 3;
q is 2 or 3;
X is O, NH, or $NR_8$;
Y is ORB, or $SR_8$;
$R_2$ and $R_3$ are independently hydrogen, unsubstituted or substituted, branched or unbranched, cyclic or acyclic aliphatic, unsubstituted or substituted, branched or unbranched, cyclic or acyclic heteroaliphatic, unsubstituted or substituted aryl or unsubstituted or substituted heteroaryl;
$R_4$, $R_5$, $R_6$, $R_7$ and $R_8$ are independently selected from hydrogen or substituted or unsubstituted, branched or unbranched, cyclic or acyclic aliphatic, and pharmaceutically acceptable forms thereof.

In one embodiment, m is 1, n is 1, q is 2, X is NH and $R_2$ and $R_3$ are unsubstituted or substituted, branched or unbranched, acyclic aliphatic. In one embodiment, $R_4$, $R_5$, $R_6$ and $R_7$ are all hydrogen.

In one embodiment, the derivative of romidepsin is of the formula (IV):

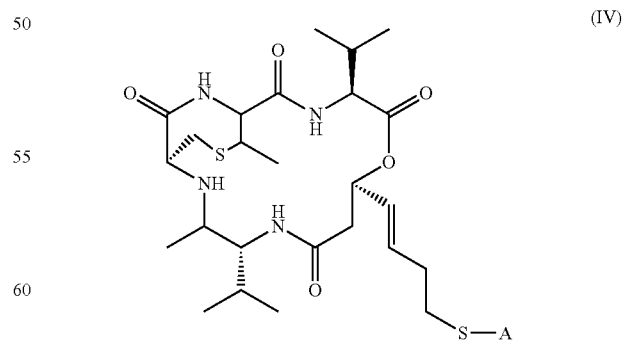

(IV)

wherein:
A is a moiety that is cleaved under physiological conditions to yield a thiol group and includes, for example, an aliphatic or aromatic acyl moiety (to form a thioester bond), an aliphatic or aromatic thioxy (to form a disulfide bond), or the like, and pharmaceutically acceptable forms thereof. Such aliphatic or aromatic groups can include a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group. A can be, for example, —COR$_1$, —SC(=O)-0-R$_1$, or —SR$_2$;

R$_1$ is independently hydrogen, substituted or unsubstituted amino, substituted or unsubstituted, branched or unbranched, cyclic or acyclic aliphatic, substituted or unsubstituted aromatic group, substituted or unsubstituted heteroaromatic group, or a substituted or unsubstituted heterocyclic group. In one embodiment, R$_1$ is hydrogen, methyl, ethyl, n-propyl, isopropyl, n-butyl, isobutyl, benzyl, or bromobenzyl;

R$_2$ is a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group. In one embodiment, R$_2$ is methyl, ethyl, 2-hydroxyethyl, isobutyl, a fatty acid, a substituted or unsubstituted benzyl, a substituted or unsubstituted aryl, cysteine, homocysteine, or glutathione.

In one embodiment, the derivatives of romidepsin are of formulae (V) or (V'):

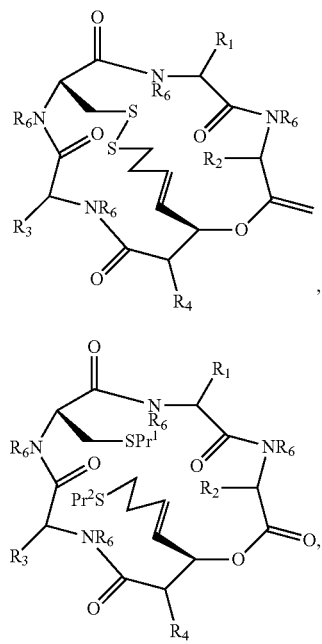

wherein:
each of R$_1$, R$_2$, R$_3$ and R$_4$ is the same or different and represent an amino acid side chain moiety;
each R$_6$ is the same or different and represents hydrogen or (C$_1$-C$_4$)alkyl; and
Pr$^1$ and Pr$^2$ are the same or different and represent hydrogen or thiol-protecting group.

In one embodiment, the amino acid side chain moieties are those derived from natural amino acids. In one embodiment, the amino acid side chain moieties are those derived from unnatural amino acids.

In one embodiment, each amino acid side chain is a moiety selected from hydrogen, (C$_1$-C$_6$)alkyl, (C$_2$-C$_6$)alkenyl, -L-O—C(0)-R', -L-C(0)-0-R", -L-A, -L-NR"R", -L-Het-C(0)-Het-R", and -L-Het-R", wherein L is a (C$_1$-C$_6$)alkylene group, A is phenyl or a 5- or 6-membered heteroaryl group, each R' is the same or different and represents (C$_1$-C$_4$)alkyl, each R" is the same or different and represent H or (C$_1$-C$_6$) alkyl, each -Het- is the same or different and is a heteroatom spacer selected from -0-, —N(R''')—, and —S—, and each R''' is the same of different and represents hydrogen or (C$_1$-C$_4$)alkyl.

In one embodiment, R$_6$ is hydrogen.

In one embodiment, Pr$^1$ and Pr$^2$ are the same or different and are selected from hydrogen and a protecting group selected from a benzyl group which is optionally substituted by (C$_1$-C$_6$)alkoxy, (C$_1$-C$_6$)acyloxy, hydroxy, nitro, picolyl, picolyl-N-oxide, anthrylmethyl, diphenylmethyl, phenyl, t-butyl, adamanthyl, (C$_1$-C$_6$)acyloxymethyl, (C$_1$-C$_6$) alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and (C$_1$-C$_6$)alkylcarbamoyl.

Various romidepsin derivatives of formula (V) and (V') are disclosed in PCT application publication WO 2006/129105, published Dec. 7, 2006, which is incorporated herein by reference.

Romidepsin Formulation

In one embodiment, romidepsin is formulated for injection as a sterile lyophilized white powder and is supplied in a single-use vial containing 10 mg romidepsin and 20 mg povidone, USP. The diluent is a sterile clear solution and is supplied in a single-use vial containing a 2 ml deliverable volume. The diluent for romidepsin contains 80% (v/v) propylene glycol, USP and 20% (v/v) dehydrated alcohol, USP. Romidepsin is supplied as a kit containing two vials.

Romidepsin for injection is intended for intravenous infusion after reconstitution with the supplied Diluent and after further dilution with 0.9% Sodium Chloride, USP.

Methods of Use

It has been found that high levels of TSPYL5 expression in a cancer patient's tumor show a high degree of correlation with resistance to treatment with an HDAC inhibitor This finding advantageously provides a significant advancement in cancer management because it allows for the identification of a patient population with increased likelihood of positive response to the treatment, by removal of patients with HDAC inhibitor resistance.

A patient found to have low levels of TSPYL5 expression relative to an expression threshold, is classified as being most likely to be responsive to an HDAC inhibitor therapy, for example, romidepsin therapy. In one embodiment, provided herein are methods for selecting a cancer patient that is a candidate for an HDAC inhibitor therapy based on a gene expression signature of TSPYL5, comprising obtaining a tumor sample from said cancer patient, quantifying the level of TSPYL5 expression in the tumor sample, wherein a low level of TSPYL5 expression, relative to an expression threshold, correlates with increased likelihood of sensitivity to the HDAC inhibitor therapy, and applying said correlation to select the cancer patient that is a candidate for the HDAC inhibitor therapy. In one embodiment, the HDAC inhibitor is romidepsin. In a further embodiment, the method encompasses the additional step of initiating HDAC inhibitor therapy for said cancer patient, for example, romidepsin therapy. In a further embodiment, the method encompasses the additional step of administering a therapeutically effective amount of an HDAC inhibitor, for example, romidepsin, to said cancer patient.

A tumor found to have high levels of TSPYL5 expression relative to an expression threshold, is classified as being most likely to be resistant to an HDAC inhibitor therapy, for example, romidepsin therapy. In one embodiment, provided herein are methods for deselecting a cancer patient at risk for resistance to an HDAC inhibitor therapy as a candidate HDAC inhibitor therapy based on a level of TSPYL5 expression, comprising obtaining a tumor sample from said cancer patient, quantifying the level of the TSPYL5 expression in the tumor sample, wherein a high level of the TSPYL5 expression, relative to an expression threshold, correlates with resistance to the HDAC inhibitor therapy, and applying said correlation to deselect the cancer patient at risk for resistance to the HDAC inhibitor therapy as a candidate HDAC inhibitor therapy. In one embodiment, the HDAC inhibitor is romidepsin.

In one embodiment, provided herein are methods for confirming therapeutic efficacy of an HDAC inhibitor therapy in a cancer patient based on a gene expression signature of the TSPYL5, comprising obtaining a tumor sample from the patient, detecting the presence of the TSPYL5 expression in the tumor sample, quantifying the level of the TSPYL5 expression in the tumor sample, wherein a low level of the TSPYL5 expression, relative to an expression threshold, correlates with increased likelihood of sensitivity to the HDAC inhibitor therapy, and applying said correlation to confirm the therapeutic efficacy of the HDAC inhibitor therapy for said cancer patient. In one embodiment, the HDAC inhibitor is romidepsin. In a further embodiment, the method encompasses the additional step of initiating HDAC inhibitor therapy for said cancer patient, for example, romidepsin therapy. In a further embodiment, the method encompasses the additional step of administering a therapeutically effective amount of an HDAC inhibitor, for example, romidepsin, to said cancer patient.

In one embodiment, provided herein are methods for predicting a lack of therapeutic efficacy of an HDAC inhibitor therapy in a cancer patient based on a gene expression signature of the TSPYL5, comprising obtaining a tumor sample from the patient, quantifying the level of the TSPYL5 expression in the tumor sample, wherein a high level of the TSPYL5 expression, relative to an expression threshold, correlates with resistance to the HDAC inhibitor therapy, and applying said correlation to predict a lack of therapeutic efficacy of the HDAC inhibitor therapy for said cancer patient. In one embodiment, the HDAC inhibitor is romidepsin.

Selection of a Patient Population

Classification of a particular patient population requires comparing the level of TSPYL5 expression in the tumor cells of a patient to an expression threshold (also referred to as basal level). This expression threshold is a level of expression of TSPYL5 that can be used to evaluate whether the level of expression of TSPYL5 in tumor cells of a patient is low or high. Specifically, when the level of TSPYL5 expression in the tumor cells of a patient is higher than the expression threshold, the cells are considered to have a high level of expression. Conversely, when the level of TSPYL5 expression in the tumor cells of a patient is lower than the expression threshold, the cells are considered to have a low level of expression. Such high or low expression is not typically calculated in terms of absolute TSPYL5 gene expression or protein levels, but is determined using relative measurements. The expression threshold may be determined by a plurality of methods and is determined in tumor cells.

The expression threshold value provides a level of TSPYL5 expression above which exists a group of patients having a different resistance to HDAC inhibitor treatment than another group of patients having TSPYL5 expression levels at or below the expression threshold. In one embodiment, the expression threshold is a level of TSPYL5 expression of in vitro cultured cells which may or may not have been manipulated to simulate tumor cells.

Expression thresholds are not necessarily the levels of TSPYL5 expression found in culture cell lines used to provide internal standards. In one embodiment, these thresholds are determined based on levels of TSPYL5 expression in tumor cells, for example, patient tumor samples.

In one embodiment, the expression threshold is determined by comparison of TSPYL5 expression levels in populations of patients having the same type of cancer. In one embodiment, it is accomplished by histogram analysis, in which the entire cohort of patients tested are graphically presented, wherein a first axis represents the levels of TSPYL5 expression, and a second axis represents the number of patients in the cohort whose tumor cells express TSPYL5 at a given level. Two or more separate groups of patients are determined by identification of subsets populations of the cohort which have the same or similar expression levels of TSPYL5. Determination of the expression thresholds is made based on an expression level which best distinguishes these separate groups.

Verification that the expression threshold distinguishes the likelihood of responsiveness to HDAC inhibitor therapy in cancer patients expressing at or below-expression thresholds of TSPYL5 versus cancer patients expressing above-expression thresholds of TSPYL5 is carried out using single variable or multivariable analysis. These methods determine the likelihood of a correlation between one or more variables and a given outcome. In one embodiment, the methods determine the likelihood of a correlation between TSPYL5 expression levels and resistance or responsiveness to HDAC inhibitor therapy. Any one of a plurality of methods well known to those of ordinary skill in the art for carrying out these analyses may be used.

In one embodiment, population-based determination of expression thresholds (i.e., histogram analysis) is carried out using a cohort of patients sufficient in size in order to determine two or more separate groups of patients having different TSPYL5 expression levels. In one embodiment, such a cohort comprises at least 10 patients. In yet another embodiment, such a cohort comprises at least 27 patients. In another embodiment, such a cohort comprises at least 100 patients. In one embodiment, verification of determined expression thresholds comprises at least 10 patients. In another embodiment, it comprises at least 50 patients. In yet another embodiment, it comprises at least 75 patients. In another embodiment, it is at least 100 patients.

In one embodiment, the expression threshold is a single value, equally applicable to every patient. In another embodiment, the expression threshold varies according to specific subpopulations of patients. For example, men might have a different expression threshold than women for the same cancer type.

In one embodiment, the expression threshold of TSPYL5 expression is used in conjunction with another variable found to be a statistically significant indicator of the likelihood of resistance to HDAC inhibitor therapy. Such indicators include, but are not limited to, clinical or pathological indicators such as age, tumor size, tumor histology, clinical stage, and the like.

The TSPYL5 expression levels can be detected or quantitated by any methods known in the art. In certain embodiments, antibody-based methods are used. In certain embodiments, the detecting or quantitating method is immunoblotting (western blot), an enzyme-linked immunosorbent assay (ELISA), immunohistochemistry, flow cytometry, a cytometric bead array, polymerase chain reaction or mass spectroscopy. In one embodiment, TSPYL5 expression levels in a tumor sample are measured using anti-TSPYL5 antibodies.

In one embodiment, a patient is classified into a group having a certain likelihood of resistance to HDAC inhibitor therapy based on determination of the level of TSPYL5 expression and comparison to an expression threshold. The likelihood of resistance to HDAC inhibitor therapy for the patient is assessed based on likelihood of resistance for patients in that group.

In one embodiment, a patient is classified into a group having a certain likelihood of responsiveness to HDAC inhibitor therapy based on determination of level of TSPYL5 expression and comparison to an expression threshold. The likelihood of responsiveness to HDAC inhibitor therapy for the patient is assessed based on likelihood of responsiveness for patients in that group.

In one embodiment, provided herein is a method for screening a cancer patient to determine the risk of resistance to an HDAC inhibitor therapy. The method comprises determining the level of TSPYL5 expression in a tumor sample or circulating tumor cell from the patient. A patient found to have high levels of TSPYL5 expression relative to an expression threshold, is classified as being most likely resistant to HDAC inhibitor therapy. In one embodiment, the HDAC inhibitor is romidepsin. In a further embodiment, the method encompasses the additional step of administering a therapeutically effective amount of a anti-cancer drug other than an HDAC inhibitor to said cancer patient.

In one embodiment, provided herein is a method for screening a cancer patient to determine the likelihood of being responsive to an anticancer therapy with HDAC inhibitor. The method comprises determining the level of TSPYL5 expression in a tumor sample or body fluid from the patient. A patient found to have low levels of TSPYL5 expression relative to an expression threshold, is classified as being most likely responsive to an HDAC inhibitor therapy. In one embodiment, the HDAC inhibitor is romidepsin. In a further embodiment, the method encompasses the additional step of administering a therapeutically effective amount of an HDAC inhibitor, for example, romidepsin, to said cancer patient.

Determination of Levels of TSPYL5 Expression

Determination of TSPYL5 expression is performed quantatively such that the level of expression can be determined. The TSPYL5 expression level is used to predict resistance of a cancer patient to the HDAC inhibitor therapy based on the correlations provided herein. In one embodiment, it has been found that when the TSPYL5 expression level is equal to or lower than an expression threshold of the TSPYL5 expression, a cancer patient is more likely to be responsive to the HDAC inhibitor therapy, for example, romidepsin therapy, compared to the average likelihood of responsiveness to HDAC inhibitor therapy calculated from a random pool of cancer patients. In another embodiment, it has been found that when the TSPYL5 expression level is higher than an expression threshold of the TSPYL5 expression, a cancer patient is likely to be resistant to the HDAC inhibitor therapy, for example, romidepsin therapy.

Nucleotide and protein sequences for human TSPYL5 can be found, for example, on the world wide web (ncbi.nlm.nih.gov) in the GenBank database maintained by the National Center for Biotechnology (NCBI) under NCBI Reference Sequence: NM_033512.2 and/or Gene-ID:85453.

In one embodiment, determination of TSPYL5 gene expression levels is performed by one or more of the methods known to one skilled in the art. In one embodiment, expression of TSPYL5 is quantified at the protein level. In one embodiment, the determination of the level of TSPYL5 expression is based on the use of an antibody. In another embodiment, expression of TSPYL5 is quantified at the RNA level.

In one embodiment, levels of TSPYL5 protein expression are detected by using antibodies, both monoclonal and polyclonal. In this embodiment, antibodies are used as specifically binding agents which bind TSPYL5 protein or a polypeptide fragment thereof. Levels of TSPYL5 expression can be measured in a tumor sample using various art known methods. For example, quantitative PCR can be used to quantify TSPYL5 expression levels in circulating tumor cells in body fluids, such as blood.

In one embodiment, one or more of the TSPYL5 specific binding agents are used in a single assay to determine TSPYL5 protein levels. A certain protein known to interact with a specific portion of the TSPYL5 protein is coupled with another specifically binding protein. Using two antibodies in a single assay, the specific levels of the differently translated TSPYL5 polypeptides are measured by differentially measuring two antibodies. Preparation of the agent for use in detection of TSPYL5 protein is carried out by the methods known to those skilled in the art (for example, the methods exemplified in the Current Protocols in Molecular Biology, John Wiley & Sons, 1999).

In another embodiment, detection of TSPYL5 protein levels is carried out by methods known to a skilled artisan, such as histochemical staining, Western Blot Analysis, or immunoprecipitation. In one embodiment, the method of detecting TSPYL5 protein levels is an immunoassay, such as ELISA, immuno-PCR, or the like.

In one embodiment, measuring levels of TSPYL5 mRNA includes detection of hybridization or amplification with the mRNA. This detection is carried out by analysis of mRNA either in vitro or in a tissue sample using one of the methods known to those skilled in the art, such as quantitative PCR, gene chip arrays, etc. (Current Protocols in Molecular Biology, supra).

In one embodiment, provided herein is an array of probes for determining the level of TSPYL5 gene expression in a tumor sample by hybridizing with one or more of the polynucleotides of TSPYL5 under stringent assay conditions; wherein the level of the TSPYL5 expression is used to identify a cancer patient at risk for resistance to HDAC inhibitor therapy.

In another embodiment, provided herein is an array of probes for determining the level of TSPYL5 gene expression in a tumor sample by hybridizing with one or more mRNAs of the TSPYL5 under stringent assay conditions, wherein the level of the TSPYL5 expression is used to identify a cancer patient at risk for resistance to HDAC inhibitor therapy.

In a further embodiment, provided herein is an array of antibodies for determining the level of TSPYL5 protein expression in a tumor sample, wherein the level of the TSPYL5 expression is used to identify a cancer patient at risk for resistance to HDAC inhibitor therapy.

Methods of Treatment

In certain embodiments, provided are methods of treating cancer. Cancer is a group of diseases which are characterized by uncontrolled growth and spread of abnormal cells. Cancers include, but are not limited to, carcinomas, sarcomas, leukemias, lymphomas and the like. In certain embodiments, cancer is a hematological malignancy. In certain embodiments, cancer is a solid tumor.

In certain embodiments the present disclosure relates to treatment of hematological malignancies. Manifestations of hematological malignancies include circulating malignant cells and malignant masses. Hematological malignancies are types of cancers that affect the blood, bone marrow, and/or lymph nodes. Hematological malignancies that may be treated using romidepsin include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), multiple myeloma, and myelodysplastic syndromes. In certain embodiments, romidepsin is used to treat multiple myeloma. In certain particular embodiments, the cancer is relapsed and/or refractory multiple myeloma. In other embodiments, romidepsin is used to treat chronic lymphocytic leukemia (CLL). In certain particular embodiments, the cancer is relapsed and/or refractory CLL. In other embodiments, romidepsin is used to treat chronic myelogenous leukemia (CML). In certain embodiments, romidepsin is used to treat acute lymphoblastic leukemia (ALL). In certain embodiments, romidepsin is used to treat acute myelogenous leukemia (AML). In certain embodiments, the cancer is cutaneous T-cell lymphoma (CTCL). In other embodiments, the cancer is peripheral T-cell lymphoma (PTCL). In certain embodiments, the cancer is a myelodysplastic syndrome.

In some embodiments of the present disclosure, cancers treated include, but are not limited to, leukemias and lymphomas such as cutaneous T-cell lymphoma (CTCL), peripheral T-cell lymphoma, lymphomas associated with human T-cell lymphotropic virus (HTLV) such as adult T-cell leukemia/lymphoma (ATLL), B-cell lymphomas, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndromes.

In some such embodiments the disclosure relates to treatment of solid tumors such as lung, breast, colon, liver, pancreas, renal, prostate, ovarian, and/or brain. In some embodiments, the disclosure relates to treatment of pancreatic cancer. In some embodiments, the disclosure relates to treatment of renal cancer. In some embodiments, the disclosure relates to treatment of prostate cancer. In some embodiments, the disclosure relates to treatment of sarcomas. In some embodiments, the disclosure relates to treatment of soft tissue sarcomas.

In some embodiments, cancers that can be treated are solid cancers that includes, but are not limited to, mesothelioma, common solid tumors of adults such as head and neck cancers (e.g., oral, laryngeal and esophageal), genitourinary cancers (e.g., prostate, bladder, renal, uterine, ovarian, testicular, rectal and colon), melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.). In certain embodiments, the cancer is melanoma. In other embodiments, the cancer is gastric cancer. In some embodiments, the disclosure relates to treatment of solid tumors.

Cancers that may be treated using the methods provided herein, including combination therapy, include but not limited to, colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, and neuroendocrine cancer.

In certain embodiments, cancer is pancreatic cancer. In certain embodiments, cancer is prostate cancer. In certain specific embodiments, the prostate cancer is hormone refractory prostate cancer.

In some particular embodiments, provided are methods to treat leukemias. In some embodiments, leukemia is chronic lymphocytic leukemia, chronic myelogenous leukemia, acute lymphocytic leukemia, acute myelogenous leukemia, or adult T cell leukemia/lymphoma.

In some embodiments, provided are methods of treating lymphomas. In some embodiments, lymphoma is Hodgkin's or non-Hodgkin's (e.g., T-cell lymphomas such as peripheral T-cell lymphoma, cutaneous T-cell lymphoma, etc.) lymphoma.

In some embodiments, the disclosure relates to the treatment of multiple myeloma and/or myelodysplastic syndromes.

An HDAC inhibitor may be administered using different routes of administration including, but not limited to, oral, rectal, transmucosal, transdermal, intestinal, and parenteral. In one embodiment, the HDAC inhibitor is romidepsin.

In one embodiment, romidepsin is administered intravenously. In one embodiment, romidepsin is administered intravenously over a time period less than about 1 hour. In one embodiment, romidepsin is administered intravenously over a 1-6 hour period. In one embodiment, romidepsin is administered intravenously over a 3-4 hour period. In one embodiment, romidepsin is administered intravenously over a 5-6 hour period. In one embodiment, romidepsin is administered intravenously over a 4 hour period.

In one embodiment, romidepsin is administered in a dose ranging from 0.5 mg/m$^2$ to 28 mg/m$^2$. In one embodiment, romidepsin is administered in a dose ranging from 0.5 mg/m$^2$ to 5 mg/m$^2$. In one embodiment, romidepsin is administered in a dose ranging from 1 mg/m$^2$ to 25 mg/m$^2$. In one embodiment, romidepsin is administered in a dose ranging from 1 mg/m$^2$ to 20 mg/m$^2$. In one embodiment, romidepsin is administered in a dose ranging from 1 mg/m$^2$ to 15 mg/m$^2$. In one embodiment, romidepsin is administered in a dose ranging from 2 mg/m$^2$ to 15 mg/m$^2$. In one embodiment, romidepsin is administered in a dose ranging from 2 mg/m$^2$ to 12 mg/m$^2$. In one embodiment, romidepsin is administered in a dose ranging from 4 mg/m$^2$ to 12 mg/m$^2$. In one embodiment, romidepsin is administered in a dose ranging from 6 mg/m$^2$ to 12 mg/m$^2$. In one embodiment, romidepsin is administered in a dose ranging from 8 mg/m$^2$ to 12 mg/m$^2$. In one embodiment, romidepsin is administered in a dose ranging from 8 mg/m$^2$ to 10 mg/m$^2$. In one embodiment, romidepsin is administered in a dose of about 8 mg/m$^2$. In one embodiment, romidepsin is administered in a dose of about 9 mg/m$^2$. In one embodiment, romidepsin is administered in a dose of about 10 mg/m$^2$. In one embodiment, romidepsin is administered in a dose of about 11 mg/m$^2$. In one embodiment, romidepsin is administered in a dose of about 12 mg/m$^2$. In one embodiment, romidepsin is administered in a dose of about 13 mg/m$^2$. In one embodiment, romidepsin is administered in a dose of about 14 mg/m$^2$. In one embodiment, romidepsin is administered in a dose of about 15 mg/m$^2$.

In one embodiment, romidepsin is administered in a dose of 14 mg/m$^2$ as an IV infusion over a 4 hour period on days 1, 8 and 15 of the 28 day cycle. In one embodiment, the cycle is repeated every 28 days.

In one embodiment, increasing doses of romidepsin are administered over the course of a cycle. In one embodiment, the dose of about 8 mg/m² followed by a dose of about 10 mg/m², followed by a dose of about 12 mg/m² is administered over a cycle.

In one embodiment, romidepsin is administered orally. In one embodiment, romidepsin is administered orally on a daily basis. In certain embodiments, romidepsin is dosed orally in the range of 10 mg/m² to 300 mg/m². In certain embodiments, romidepsin is dosed orally in the range of 25 mg/m² to 100 mg/m². In certain embodiments, romidepsin is dosed orally in the range of 100 mg/m² to 200 mg/m². In certain embodiments, romidepsin is dosed orally in the range of 200 mg/m² to 300 mg/m². In certain embodiments, romidepsin is dosed orally at greater than 300 mg/m². In certain embodiments, romidepsin is dosed orally in the range of 50 mg/m² to 150 mg/m². In other embodiments, the oral dosage ranges from 25 mg/m² to 75 mg/m². In one embodiment, romidepsin is administered orally every other day. In one embodiment, romidepsin is administered orally every third, fourth, fifth, or sixth day. In one embodiment, romidepsin is administered orally every week. In one embodiment, romidepsin is administered orally every other week.

In one embodiment, romidepsin is administered orally in a dose of 50 mg/m² on days 1, 8 and 15 of the 28 day cycle. In one embodiment, the cycle is repeated every 28 days.

In one embodiment, increasing doses of romidepsin are administered over the course of a cycle. In one embodiment, the dose of about 25 mg/m² followed by a dose of about 50 mg/m², followed by a dose of about 75 mg/m² is administered over a cycle.

In one embodiment, one cycle comprises the administration of from about 25 to about 150 mg/m² of romidepsin daily for three to four weeks and then one or two weeks of rest. In one embodiment, the number of cycles during which the treatment is administered to a patient will be from about one to about 40 cycles, or from about one to about 24 cycles, or from about two to about 16 cycles, or from about four to about three cycles.

Dosing

In some embodiments, romidepsin and/or compositions comprising romidepsin are administered according to a standard dosing regimen. In some embodiments, romidepsin and/or compositions comprising romidepsin are administered according to an accelerated dosing regimen.

Standard Dosing for Romidepsin

In some embodiments, unit doses of romidepsin are within the range of about 0.5 mg/m² to about 28 mg/m² body surface area. In some embodiments, the range of about 6 mg/m² to about 18 mg/m² is used. In some embodiments, the range is about 10 mg/m² to about 17 mg/m². In some embodiments, particular unit doses are 10 mg/m², 12 mg/m², 13 mg/m², 14 mg/m², and 15 mg/m².

In some embodiments, intravenous dosing regimens include daily dosing for 2 weeks, twice weekly dosing for 4 weeks, thrice weekly dosing for 4 weeks, and various other intermittent schedules (e.g., on days 1, 3, and 5; on days 4 and 10; on days 1, 8 and 15; on days 1 and 15; on days 5 and 12; or on days 5, 12, and 19 of 21 or 28 day cycles).

In some embodiments, romidepsin is administered in individual unit doses over 4 hours on days 1, 8, and 15, with courses repeating every 28 days. Often, several courses (e.g., at least 4, at least 6, or more) are administered. Indeed, instances have been reported of as many as 72 courses being administered. In some embodiments, individual unit doses are administered by 4 hour infusion.

Accelerated Dosing for Romidepsin

Accelerated dosing regimens for romidepsin may be utilized, in which one or more individual unit doses is administered intravenously over a period of time that is less than or equal to about one hour. In some embodiments, one or more individual doses are administered intravenously over a period of time that is less than about 50 minutes, 40 minutes, 30 minutes, 20 minutes, or less. Any regimen that includes at least one unit dose administered over a period of time that is less than about one hour (60 minutes) may be considered an accelerated dosing regimen in accordance with the present disclosure.

In some embodiments, all unit doses within a regimen are administered intravenously over a time period that is less than or equal to about one hour. In some embodiments, only some of the unit doses within a regimen are administered over a time period that is less than or equal to about one hour. In some embodiments, one or more unit doses within a regimen are administered by a route other than intravenous administration (e.g., oral, subcutaneous, nasal, topical, etc.).

Accelerated dosing regimens of romidepsin can be administered without a significant increase in toxicity or adverse events, particularly in serious adverse events, as compared with a comparable regimen (e.g., an otherwise identical regimen) in which individual unit doses are administered intravenously over a 4-hour period. In one embodiment, accelerated dosing regimens can be administered without a significant increase in toxicity or adverse events, particularly in serious adverse events, as compared with a standard regimen of romidepsin administered by 4-hour intravenous infusion of a dose of about 6-14 mg/m² on days 1, 8, and 15 of a 28 day cycle.

In some embodiments, romidepsin is administered in an accelerated dosing regimen that is identical to a standard dosing regimen except that one or more unit doses is administered over a time period that is less than about 1 hour (e.g., rather than over a time period of about 4 hours).

As will be appreciated by one of skill in the art, the dosage, timing and/or routes of administration of particular unit doses of romidepsin may vary depending on the patient and condition being treated. In certain embodiments, the cycles are continued as long as the patient is responding. Therapy may be terminated once there is disease progression, a cure or remission is achieved, or side effects become intolerable. Adverse side effects may also call for lowering the dosage of romidepsin administered, or for adjusting the schedule by which doses are administered.

Pharmaceutical Formulations

In one embodiment, provided herein are pharmaceutical formulations, which comprise romidepsin, or a pharmaceutically acceptable salt or solvate thereof, as an active ingredient, in combination with one or more pharmaceutically acceptable carrier. In one embodiment, the pharmaceutical composition comprises at least one nonrelease controlling excipient or carrier. In one embodiment, the pharmaceutical composition comprises at least one release controlling and at least one nonrelease controlling excipients or carriers.

In certain embodiments, romidepsin used in the pharmaceutical compositions provided herein is in a solid form. Suitable solid forms include, but are not limited to, solid forms comprising romidepsin, and solid forms comprising salts of romidepsin. In certain embodiments, solid forms provided herein include polymorphs, solvates (including hydrates), and cocrystals comprising romidepsin and/or salts thereof. In certain embodiments, the solid form is an amorphous form of romidepsin, or a pharmaceutically acceptable salt or solvate thereof.

In one embodiment, the pharmaceutical compositions provided herein may be formulated in various dosage forms for parenteral administration. In one embodiment, the pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In some embodiments, the composition is prepared by lyophilization from a solution. In particular embodiments, the composition is prepared by lyophilization from a solution of t-butanol and water. In some embodiments, the solvent is tert-butanol. In some embodiments, the solvent is a mixture of tert-butanol and water. In some embodiments, the solution is (60:40) (v/v) of t-butanol and water. In some embodiments, the pH adjustor is inorganic acid. In one embodiment, the inorganic acid is hydrochloric acid.

Parenteral Administration

In one embodiment, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In one embodiment, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy*, supra).

In one embodiment, the pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, the pharmaceutical compositions provided herein may be formulated for single or multiple dosage administration. The single dosage formulations are packaged in an ampoule, a vial, or a syringe. The multiple dosage parenteral formulations may contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions may be formulated as a suspension, solid, semi-solid, or thixotropic liquid, for administration as an implanted depot.

In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyloxyethanol copolymer, and ethylene/vinyl acetate/vinyl alcohol terpolymer.

Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

Kits

In one embodiment, a kit comprises a container filled with an HDAC inhibitor, reagents for detecting the TSPYL5 gene and/or protein, and instructions for detecting the level of expression of the TSPYL5 gene and/or protein in a patient having cancer.

In certain embodiments, the kit comprises one or more probes that bind specifically to the TSPYL5 mRNAs. In certain embodiments, the kit further comprises a washing solution. In certain embodiments, the kit further comprises reagents for performing a hybridization assay, TSPYL5 mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the TSPYL5 protein level. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample.

In one embodiment, a kit comprises a dosage form of romidepsin. Kits can further comprise a pharmacologically active derivative of romidepsin.

In other embodiments, kits can further comprise devices that are used to administer the active ingredients. Examples of such devices include, but are not limited to, syringes, and drip bags.

In one embodiment, kits can further comprise a pharmaceutically acceptable vehicle that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Unless otherwise defined, all technical and scientific terms used herein are accorded the meaning commonly known to one of skill in the art. All publications, patents, published patent applications, and other references mentioned herein are hereby incorporated by reference in their entirety. The embodiments of the disclosure should not be deemed to be mutually exclusive and can be combined.

EXAMPLES

The following examples are provided by way of illustration, not limitation.

Example 1

Definition and Calculation of S-value

Sensitivity of cells to HDAC inhibitor treatment is expressed as their S-value (S), which is a dimensionless compound value generated by adding the values of $IC_{50}$ and the growth rate (GR) at the maximum drug concentration used to determine the $IC_{50}$. The term (maximum drug concentration/200) is added in the equation below to achieve equal weighting of the S-value for $IC_{50}$ and GR.

$$S=IC_{50}+(GR+100)\times(\text{maximum drug concentration}/200)$$

See FIG. 1 for an example of an S value calculation and explanation of GR.

The S-Value is highly correlated with the Area Under the Curve (AUC) value obtained from inhibition vs. compound concentration graph, and these two values can be used interchangeably.

To determine cell growth $IC_{50}$ and GR at a given drug concentration, growth was plotted against drug concentration as a percentage of the number of cells present at the beginning of the experiment. Cells were plated in 96-well plates and allowed to attach and grow overnight. The following day, the cells were treated with serial dilutions of test compound. The viable cells were measured at day 0 (24 hours after plating) and day 3 (72 hours after adding the tested compound) using Cell Titer-Glo. Growth was calculated compared to day 0. Explanation sample graph is presented in FIG. 1.

The plot generated two key data, the $IC_{50}$ value and the % growth at the highest tested compound concentration (GR). The highest concentration tested for romidepsin was 1000 nM.

The $IC_{50}$s in these experiments could range from 0-1000 nM. A given $IC_{50}$ value, 97.35 nM as shown in the sample plot (FIG. 1), was added as its numerical value in the calculation of the S-value, 97.35 (FIG. 1). Growth at the highest drug concentration tested ranged from −100 to +100. For the calculation of the S-Value, 100 was added to the numerical value of the observed growth, so that only positive numbers were generated (after adding 100, the range was from 0-200). Since $IC_{50}$s and growth at the maximum drug concentration tested have different numerical ranges (0-1000 as compared to 0-200), the value for growth inhibition was multiplied by the maximum drug concentration used/200. This means that in the example given, both $IC_{50}$ and GR could contribute values of 0-1000 to the S-value.

See FIG. 1:

$$S\text{-Value} = IC_{50} + (\text{Growth inhibition at } 1000 \text{ nM} + 100) \times 5$$
$$= 97.35 + (-79.5 + 100) \times 5 = 199.85.$$

Example 2

Sensitivity to Romidepsin in Various Cell Lines

Figure 2A:
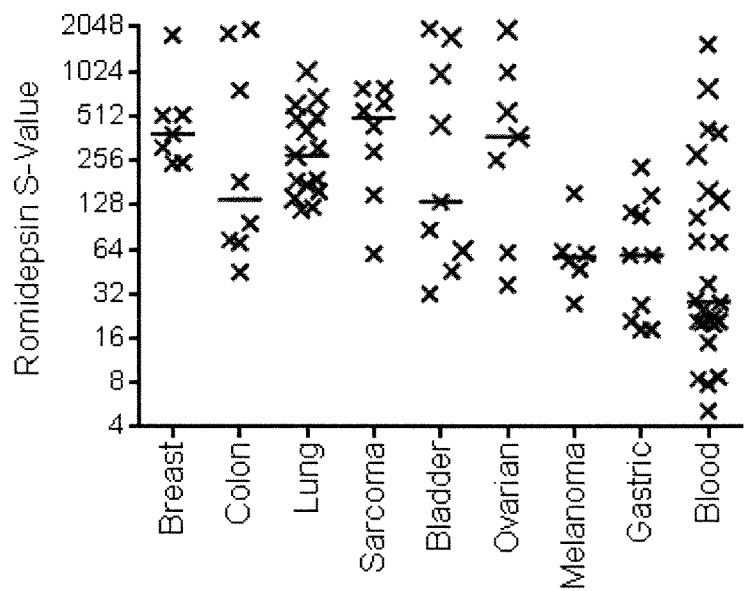
FIG. 2A shows romidepsin S-values in different cell lines as a whisker plot. Sensitivity of cell lines to romidepsin treatment was determined using 6 h drug treatment and is expressed using the S value. The lower the value, the more sensitive the cell line is to romidepsin treatment. Cell lines are grouped according to their tissue of origin, and for each cell line, the romidpsin S value is plotted against the tissue of origin. The sensitivity of the cell lines varies greatly, with S values ranging from 4-2000.
Figure 2B:
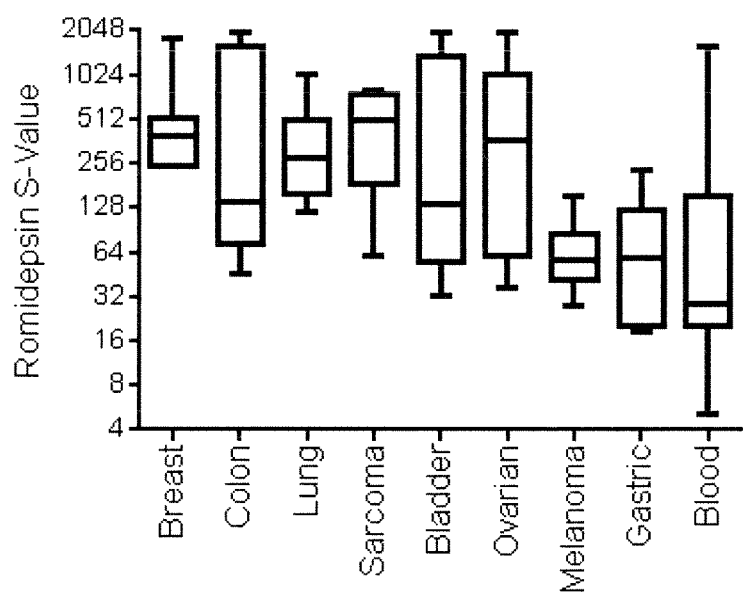
FIG. 2B demonstrates the sensitivity distribution in various cell lines based on the S-Value using a box plot showing the smallest observation (sample minimum), lower quartile (Q1), median (Q2), upper quartile (Q3), and largest observation (sample maximum). Sensitivity of cell lines to romidepsin treatment was determined using 6 h drug treatment and is expressed using the S value. The lower the value, the more sensitive the cell line is to romidepsin treatment. Cell lines are grouped according to their tissue of origin, and cell line origin is plotted against the romidepsin S value. Sensitivity of different types of cancer cell lines to romidepsin varies greatly. As shown here, blood cell lines show the greatest sensitivity.

A cell line panel viability screen was used to compare the effects of a 6 hour and 72 hour treatment with romidepsin across a wide variety of cell lines. Although the majority of the tested cell lines showed sensitivity to romidepsin in the 72 hour assay, the 6 hour exposure revealed significant differences in sensitivity to romidepsin in various cell lines. The S-Value was computed for the 6 h treatment and ranged from 5 for the most sensitive cell lines to 2000 for the most resistant cell lines. The results are shown in FIGS. 2A and 2B. To identify genes whose expression correlated with sensitivity to HDAC inhibitor treatment, we applied two way ANOVA to select genes that were correlated with sensitivity. We used 24 solid tumor cell lines of breast, colon and ovary origin, since lines from these 3 tumor types had a large spread of S values, and identified 254 unique probes that were significantly different between these two groups. The most overexpressed gene in the resistant subgroup, ABCB1 (Res/Sen=29.6) is known to cause resistance to romidepsin treatment. This approach identified novel genes that correlated with resistance and/or sensitivity to the HDAC inhibitors but not tissue origin. Using this approach, it was found that the expression of the TSPYL5 gene correlated with resistance to romidepsin.

Example 3

TSPYL5 Expression Correlates with Resistance to Romidepsin in Cell Line Screen

Figure 3:
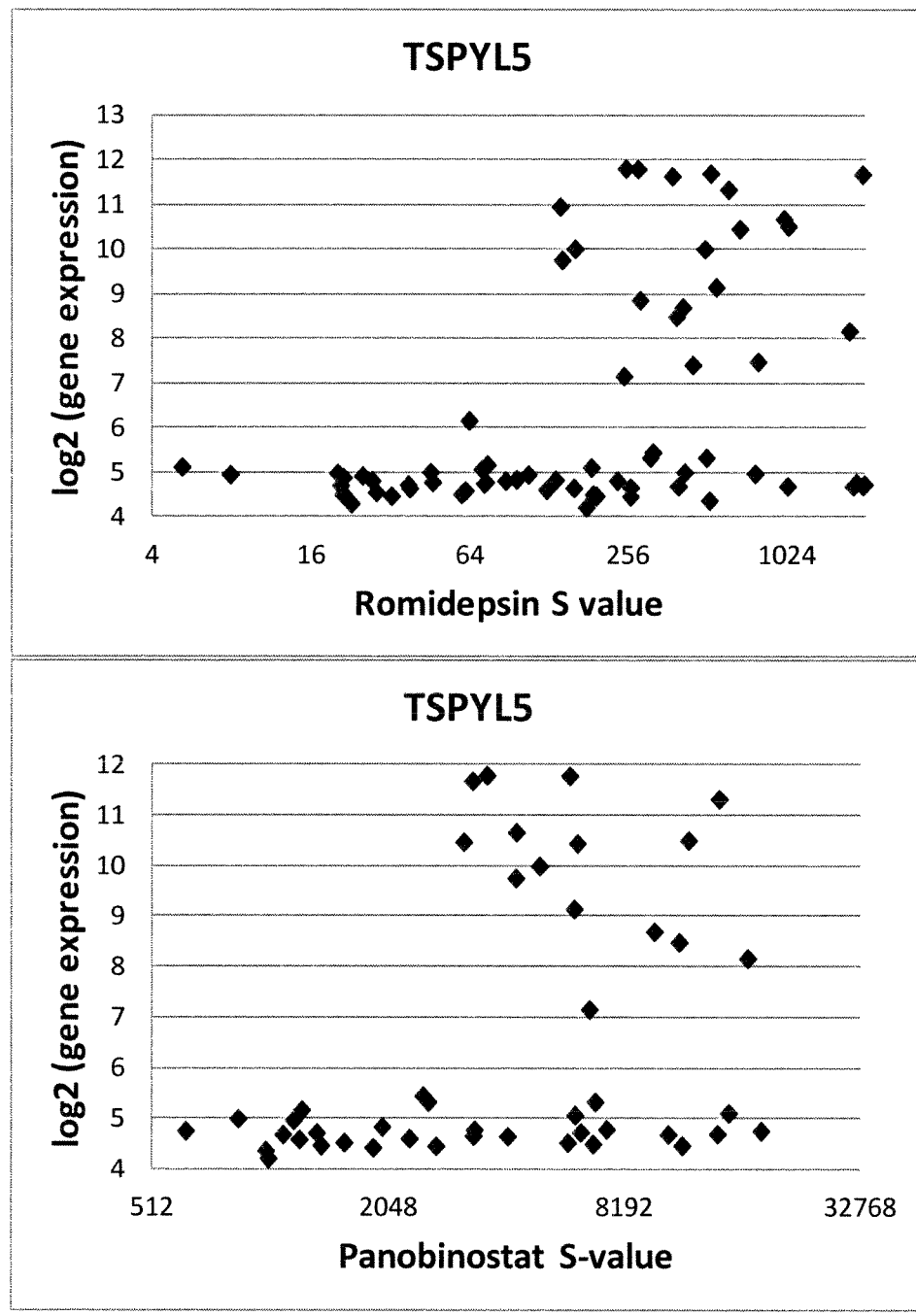
FIG. 3 depicts the correlation between TSPYL5 gene expression and S-values in a cell line screen. Gene expression of TSPYL5 was quantified in a set of cell lines using an Affymetrix gene profiling array and plotted against the sensitivity of the cell line to either romidepsin (left plot) or panobinostat (right plot) as measured by their S value. The lower the S value, the higher the sensitivity to drug treatment. Cells lines with more than baseline expression of TSPYL5 have high S values, that is, they are resistant to treatment with either romidepsin or with panobinostat.

A cell line panel viability screen was used to compare the effects of romidepsin across a wide variety of cell lines and is shown in FIG. 3.

The data indicates that the expression of TSPYL5 correlated with resistance to romidepsin in the tested cell lines. It was demonstrated that no cell line expressing high levels of TSPYL5 was sensitive to treatment with romidepsin or panobinostat, while all cell lines sensitive to treatment with these two HDAC inhibitors had baseline expression of TSPYL5.

Example 4

TSPYL5 Expression Correlates with Resistance to Romidepsin in Primary Patient Tumor Explants Primary human tumors were propagated in mice. Tumors were dissociated and their sensitivity to romidepsin was tested using a clonogenic assay.

The clonogenic assay was performed in a 24-well format according to a modified two-layer soft agar assay introduced by Hamburger & Salmon (Hamburger A W, Salmon S E. Primary bioassay of human tumor stem cells. Science 197: 461 (1977)). Briefly, cells were seeded on a bottom layer of growth medium supplemented with 0.4% (w/v) agar. Cells were added in 0.2 ml of the same medium supplemented with 0.4% (w/v) agar. Test compounds were applied diluted in culture medium. Cultures were incubated at 37° C. and 7.5% $CO_2$ in a humidified atmosphere for up to 21 days. After 4-21 days, colonies were counted and drug effect was expressed as percent colony formations compared to untreated controls.

Figure 4:
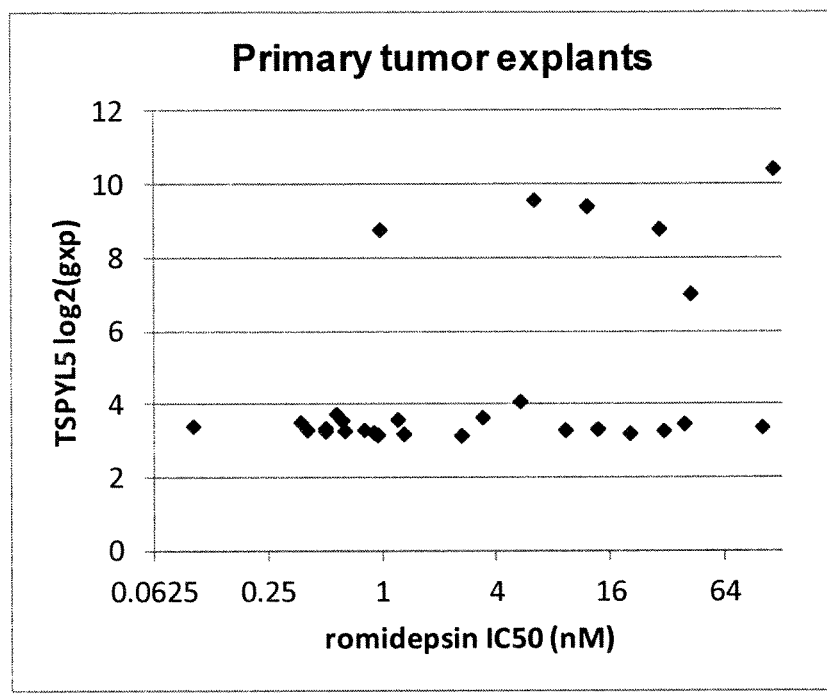
FIG. 4 depicts the correlation between TSPYL5 gene expression and the $IC_{50}$ value of romidepsin in primary patient tumors explants. Romidepsin resistance of primary tumors correlates with TSPYL5 expression. Human primary tumors were propagated in mice. For $IC_{50}$ measurements, tumors were dissociated and grown in a clonogenic assay in the presence of different concentrations of romidepsin. The graph plots TSPYL5 expression of the primary tumors against romidepsin $IC_{50}$ as determined in the clonogenic assays. Primary tumors with high TSPYL5 expression have relatively high $IC_{50}$s.

The graph shown in FIG. 4 shows the expression of TSPYL5 against the romidepsin $IC_{50}$ obtained with the clonogenic assay. Primary tumors with high TSPYL5 expression were resistant to treatment with romidepsin.

Example 5

Effect of Knockdown of TSPYL5 on Sensitivity to Romidepsin

It was shown that knockdown of TSPYL5 expression increased sensitivity to romidepsin treatment. Results are shown in Table 1 below and in FIG. 5.

TABLE 1

Knockdown of TSPYL5 in SKOV3 cells with shRNA increases sensitivity to romidepsin

| Cell line | IC50, nM | GR, % | S value |
|---|---|---|---|
| SKOV3 TSPYL5 KD | 58 | −88.6 | 115 |
| | 71 | −93.2 | 105 |
| | 43 | −86.1 | 112 |
| | 57 | −84.3 | 135 |
| | 118 | −92.5 | 156 |
| SKOV3 NS | 141 | −70 | 291 |
| | 136 | −76.5 | 253 |
| | 139 | −76.6 | 256 |
| | 98 | −73.5 | 230 |
| | 162 | −85.1 | 243 |

Effect of knocking down TSPYL5 expression using shRNA on $IC_{50}$, GR and S values of romidepsin treatment. SKOV3 cells expressing either TSPYL5 shRNA (SKOV3 TSPYL5 KD) or non-silencing control shRNA (SKOV3 NS) were created using lentiviral infection. Knockdown of TSPYL5 in SKOV3 TSPYL5 KD cells was verified using western blot and quantitative PCR. Expression of TSPYL5 in these cells was reduced by 70%. After selection of stable pools with puromycin, cells were treated with varying concentrations of romidepsin for determination of $IC_{50}$, GR and S value. Data from 5 independent experiments are shown. SKOV3 TSPYL5 KD cells have lower $IC_{50}$s, show stronger growth rate (GR) and have thus smaller S values than SKOV3 NS cells, meaning these cells are more sensitive to treatment with romidepsin. The data are plotted in FIG. 5. Differences between the 2 lines are significant (paired t test).

Example 6

Effect of Knockdown of TSPYL5 on Sensitivity to Panobinostat

Figure 7A:
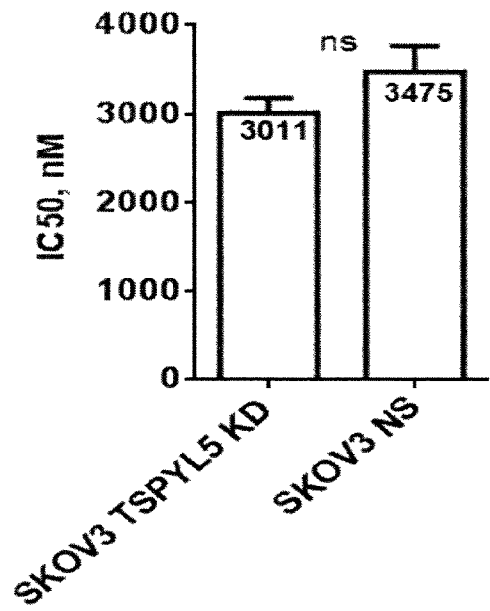
FIG. 7 depicts the effect of knockdown of TSPYL5 expression on sensitivity of SKOV-3 cells to panobinostat using shRNA, as measured by the effect of panobionstat treatment on IC50 (Panel A), growth rate (GR) (Panel B) and S value (Panel C). Sensitivity of TSPYL5 knockdown cells to panobinostat is increased as measured by S value and growth rate. SKOV3 cells expressing either TSPYL5 shRNA (SKOV3 TSPYL5 KD) or non-silencing control shRNA (SKOV3 NS) were created using lentiviral infection. Knockdown of TSPYL5 in SKOV3 TSPYL5 KD cells was verified using western blot (data not shown) and quantitative PCR. Expression of TSPYL5 in these cells was reduced by 70%. After selection of stable pools with puromycen, cells were treated with varying concentrations of panobinostat for determination of $IC_{50}$, GR and S value. The data shown are means and standard deviations from 5 independent experiments. Panel A: panobinostat $IC_{50}$s for SKOV3 TSPYL5 KD cells and SKOV3 NS cells. Panel B: panobinostat GR for SKOV3 TSPYL5 KD cells and SKOV3 NS cells. Panel C: panobinostat S value for SKOV3 TSPYL5 KD cells and SKOV3 NS cells. Numbers in white are means obtained from 5 experiments. The asterisks describe values levels of statistical significance, with 1 asterisks depicting p-values between 0.01 and 0.05.
Figure 7B:
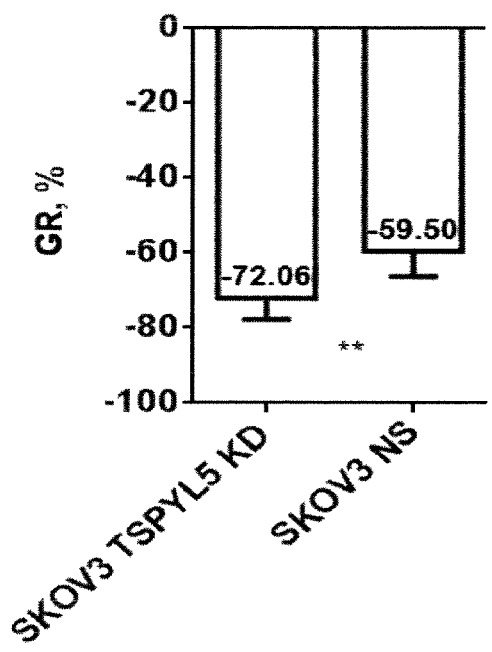
Figure 7C:
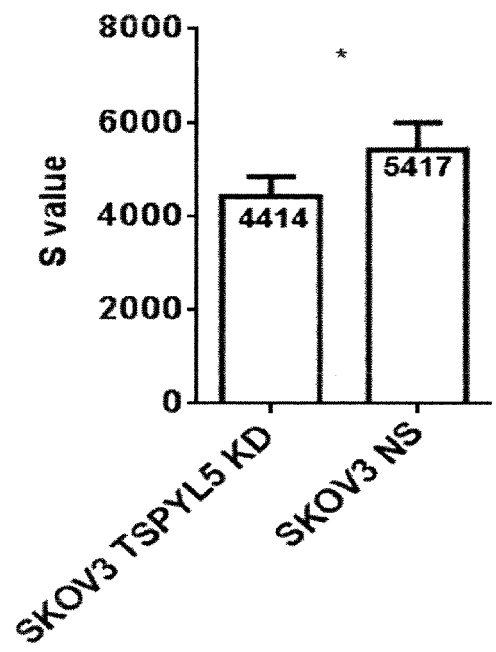

It was shown that knockdown of TSPYL5 with shRNA increases sensitivity of SKOV3 cells to panobinostat treatment. The results are shown in FIG. 7.

Example 7

Figure 8A:
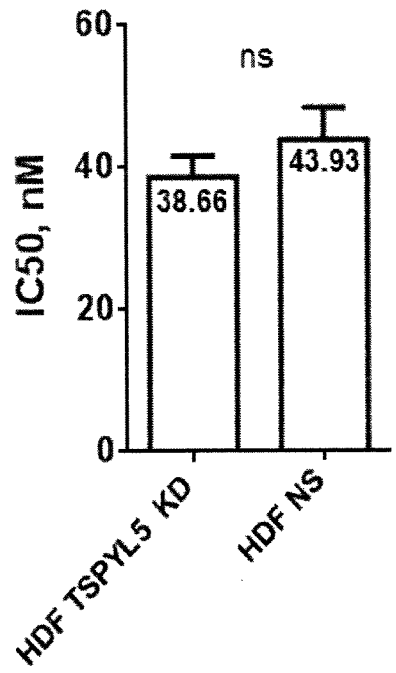
FIG. 8 depicts the effect of knockdown of TSPYL5 expression on sensitivity of HDF cells to romidepsin using shRNA, as measured by the effect of romidepsin treatment on $IC_{50}$ (Panel A), growth rate (GR) (Panel B) and S value (Panel C). Sensitivity of TSPYL5 knockdown cells to romidepsin is increased as measured by S value and growth rate. HDF cells expressing either TSPYL5 shRNA (HDF TSPYL5 KD) or non-silencing control shRNA (HDF NS) were created using lentiviral infection. Knockdown of TSPYL5 in HDF TSPYL5 KD cells was verified using western blot and quantitative PCR. Expression of TSPYL5 in these cells was reduced by >70%. After selection of stable pools with puromycen, cells were treated with varying concentrations of romidepsin for determination of $IC_{50}$, GR and S value. The data shown are means and standard deviations from 8 independent experiments. Panel A: Romidepsin $IC_{50}$s for HDF TSPYL5 KD cells and HDF NS cells. Panel B: Romidepsin GR for HDF TSPYL5 KD cells and HDF NS cells. Panel C: Romidepsin S value for HDF TSPYL5 KD cells and HDF NS cells. Numbers in white are means obtained from 8 experiments. The asterisks describe values levels of statistical significance, with 2 asterisks depicting p-values between 0.001 and 0.01.
Figure 8B:
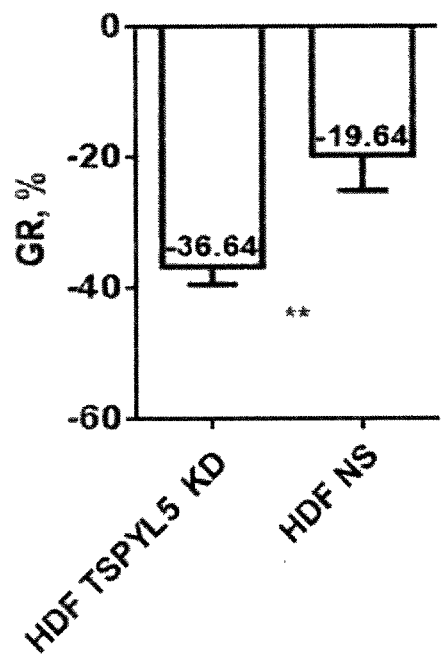
Figure 8C:
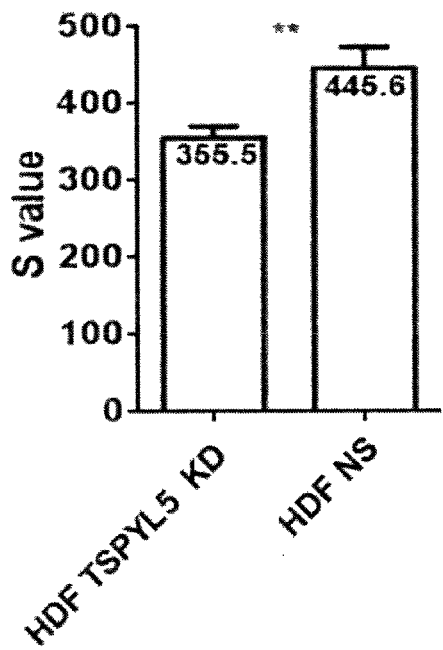

Effect of Knockdown of TSPYL5 on Sensitivity of Human Dermal Fibroblasts to Romidepsin It was shown that knockdown of TSPYL5 with shRNA increases sensitivity of human dermal fibroblast (HDF) cells to romidepsin treatment. The results are shown in FIG. 8.

All publications, patents, and patent applications mentioned in this specification are herein incorporated by reference to the same extent as if each individual publication, patent, or patent application was specifically and individually indicated to be incorporated by reference.

The present disclosure has been described above with reference to exemplary embodiments. However, those skilled in the art, having read this disclosure, will recognize that changes and modifications may be made to the exemplary embodiments without departing from the scope of the present disclosure. The changes or modifications are intended to be included within the scope of the present disclosure, as expressed in the following claims.

The invention claimed is:

1. A method for identifying a cancer patient with an increased likelihood of a positive clinical response to romidepsin therapy comprising:

obtaining a tumor sample from the cancer patient;
detecting the presence of TSPYL5 expression in said sample;
quantifying a level of said TSPYL5 expression in said sample; and
administering a therapeutically effective amount of romidepsin upon a determination that TSPYL5 expression in said sample is lower than a defined expression threshold.

2. The method of claim 1, wherein the level of the TSPYL5 expression is determined by measuring the amount of TSPYL5 protein using an immunoassay.

3. The method of claim 2, wherein the immunoassay is an immune-polymerase chain reaction (immuno-PCR).

* * * * *